(12) United States Patent
Karling et al.

(10) Patent No.: US 8,332,999 B2
(45) Date of Patent: Dec. 18, 2012

(54) METHOD AND DEVICE FOR SECURELY LOADING AND MOUNTING A TUBULAR DEVICE IN A FLEXIBLE WALL AND MANUFACTURING METHOD FOR SAID LOADING DEVICE

(75) Inventors: Jonas Karling, Nacka (SE); Gregory Margolin, Stockholm (SE)

(73) Assignee: Atos Medical AB (SE)

( * ) Notice: Subject to any disclaimer, the term of this patent is extended or adjusted under 35 U.S.C. 154(b) by 1165 days.

(21) Appl. No.: 11/547,685

(22) PCT Filed: Apr. 8, 2005

(86) PCT No.: PCT/SE2005/000521
§ 371 (c)(1),
(2), (4) Date: Dec. 22, 2008

(87) PCT Pub. No.: WO2005/097001
PCT Pub. Date: Oct. 20, 2005

(65) Prior Publication Data
US 2009/0102180 A1    Apr. 23, 2009

(30) Foreign Application Priority Data
Apr. 8, 2004   (SE) ...................................... 0400943

(51) Int. Cl.
*B23P 11/00* (2006.01)
*A61F 2/20* (2006.01)
*A62B 9/02* (2006.01)
*A62B 9/06* (2006.01)
*F16B 17/00* (2006.01)

(52) U.S. Cl. ........................ 29/243.5; 623/9; 128/207.16
(58) Field of Classification Search ................. 29/243.5; 623/9; 128/207.14, 207.16, 207.17
See application file for complete search history.

(56) References Cited

U.S. PATENT DOCUMENTS

| | | | |
|---|---|---|---|
| 4,494,252 A * | 1/1985 | Chaoui | 623/9 |
| 5,064,433 A * | 11/1991 | Blom et al. | 623/9 |
| 5,571,180 A * | 11/1996 | Blom | 623/9 |
| 5,935,165 A * | 8/1999 | Schouwenburg | 623/9 |
| 5,976,151 A * | 11/1999 | Siegbahn | 606/108 |
| RE39,923 E * | 11/2007 | Blom | 623/9 |
| 7,909,868 B2 * | 3/2011 | Blom | 623/9 |
| 2008/0216839 A1 * | 9/2008 | Rutter | 128/207.14 |

* cited by examiner

*Primary Examiner* — Lee D Wilson
*Assistant Examiner* — Alvin Grant
(74) *Attorney, Agent, or Firm* — Rader, Fishman & Grauer PLLC

(57) ABSTRACT

An improved method and device for securely inserting a tubular element (30) into a through-aperture (40) in a flexible wall (60) accessible from one side only. The tubular element has a retainer (31, 32) projecting transversely at each end thereof, said retainer being resiliently foldable towards the axis of said tubular element. The element is inserted into a loading tube (11), wherein the retainers are automatically folded into the correct orientation by an automatic bending means (18). The bending means is part of a self-contained device for inserting said tubular element (30) into said through-aperture (40).

18 Claims, 16 Drawing Sheets

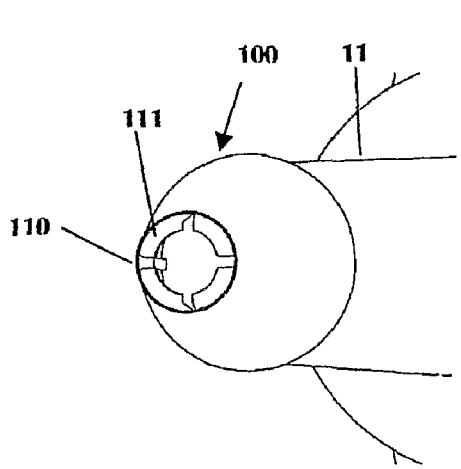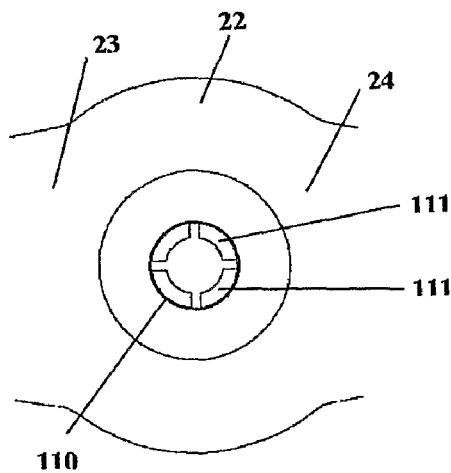
Fig. 18A  Fig. 18B
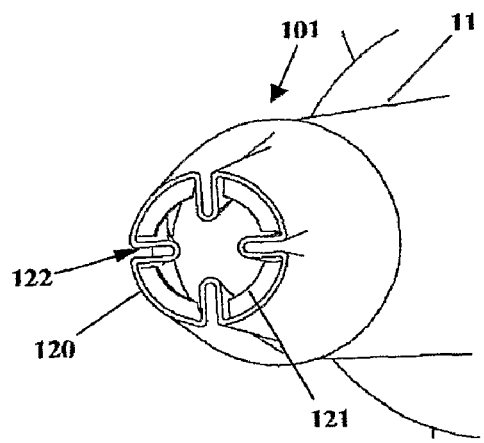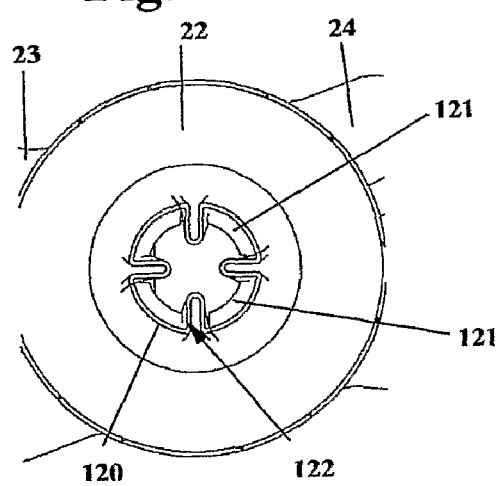
Fig. 19A  Fig. 19B
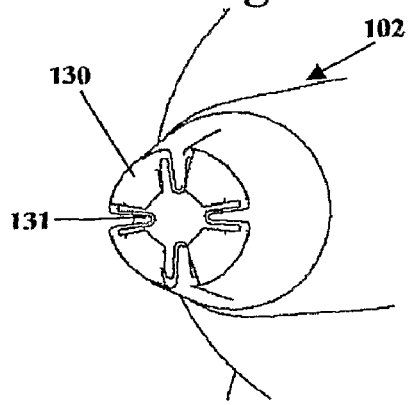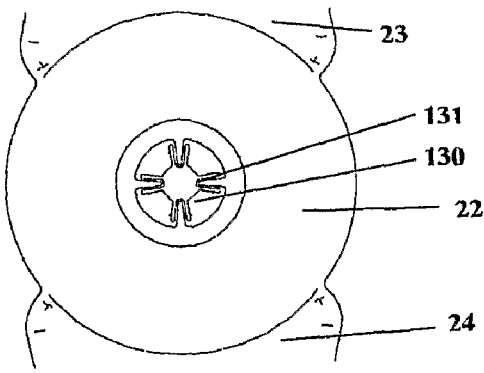
Fig. 20A  Fig. 20B

METHOD AND DEVICE FOR SECURELY LOADING AND MOUNTING A TUBULAR DEVICE IN A FLEXIBLE WALL AND MANUFACTURING METHOD FOR SAID LOADING DEVICE

FIELD OF THE INVENTION

The invention pertains in general to a method and a device for inserting a tubular element having a retainer projecting transversely at each end thereof, said retainer being resiliently foldable towards the axis of said tubular element, into a through aperture in a flexible wall accessible from one side only. Furthermore, the invention concerns a method of manufacturing such a device.

BACKGROUND OF THE INVENTION

There may be a need of mounting in products of flexible material such as inflatable objects, or hoses of coated fabric or rubber material, tubular elements of different kinds for example bushings, connectors, or valves, in a flexible wall which is accessible from one side only.

EP-B1-0868291 discloses a method and device for mounting a tubular element in a flexible wall using a loading tube and a tool inserted therein supporting the tubular element during delivery through the loading tube. Although the method and device are well proven for use by professionally trained personal, the method and device may be improved for less trained operators. There is a need for improving the insertion of the tubular device into a loading tube. Especially the reliability and convenience of bending retainers into an axially orientation, from initially projecting transversely, at each end of the tubular device when pushing the device into a loading tube may be improved. This step is hitherto performed manually by an operator of the loading tube, wherein this step, likewise all manually performed operations, underlies fluctuations in reliability of the step performed. Potential sources of errors are for instance the orientation of the retainers when loaded into the loading tube, the rotational orientation of the tubular device in the loading tube and thus in the flexible wall when mounted into the wall, or contamination of the tubular device with undesired contaminants. There is also a need for such a loading device and method being operable by a more simpler manipulation of a smart inserting device, for instance a one-hand operation.

Hence, an improved mounting device would be advantageous. The purpose of the invention is to facilitate such mounting of a tubular device and to improve the ease-of-use of a loading device used for said mounting, as well as improving the security and reliability of the mounting. The invention seeks also to solve the problem of manufacturing such an improved loading device.

SUMMARY OF THE INVENTION

Accordingly, the present invention preferably seeks to mitigate, alleviate or eliminate one or more of the above-identified deficiencies in the art and disadvantages singly or in any combination and solves at least the above mentioned problems at least partly by providing an improved loading method and loading device as well as a manufacturing method for said loading device according to the appended independent claims within the inventive concept of the present invention.

According to one aspect of the invention, a method is provided in the appended independent method claim. The preamble of this claim is based on EP-B1-0868291 and refers to a method for inserting a tubular element into a through-aperture in a flexible wall that is accessible from one side only. The tubular element forms a central passage and has a retainer projecting transversely at each end thereof. The retainers are resiliently foldable towards the longitudinal axis of the tubular element. In order to achieve the above-mentioned purposes, the method has obtained the characterising features of the appended independent method claim. More precisely, the tubular element is passed into a loading tube by automatically radially and axially displacing a first of said retainers by means of a bending means into a folded position, such that the retainers substantially project axially in direction of the longitudinal axis and in insertion direction from a first end of the element.

The method of the invention may also be applied for inserting a voice prosthesis, i.e. a low-resistance indwelling device for prosthetic voice rehabilitation after total laryngectomy, which is inserted in a tracheoesophageal fistula. A voice prosthesis of this type is disclosed in U.S. Pat. No. 5,314,470.

According to another aspect of the invention, a self-contained loading device is provided according to the appended device claim. The device is of the type disclosed in EP-B1-0868291 and comprises a loading tube for receiving the tubular element therein with the retainers thereof folded and projecting axially from the element, and a tool to be received in the loading tube to be engaged with the tubular element therein, said loading tube and said tool being relatively displaceable for pushing the element out of the loading tube. Within the inventive concept, the loading device has obtained the characterising features of the appended independent device claim. More precisely the loading device comprises a bending means for bending the retainers into the desired orientations. The tubular element is according to an embodiment attached to said bending means providing a first assembly that is releasably mounted to the tool at one end thereof, thus providing a second assembly. The second assembly is positioned in a loading section of the loading tube with said tool partly protruding out of a guide cover attached to said loading section. The loading device is preferably used for practising the method of the invention.

According to a further aspect of the invention, a manufacturing method for the above-mentioned self-contained loading device is provided within the present inventive concept. The manufacturing method of an embodiment of the invention is characterised by the steps of releasably loading said tubular element into a central passage of a bending means, said retainers extending substantially radially outwards on each side of said bending means, providing a first assembly. Further this first assembly is releasably mounted to a tool at one end thereof, providing a second assembly. Then the second assembly is inserted axially into a loading section of a loading tube. A guiding cover is pushed over and passed along the tool via a central guiding passage in said guiding cover, and the guiding cover is attached to said loading section.

The present invention provides the advantage over the prior art that it offers improved security of the mounting process, in combination with improved user-friendliness and a ready to use self contained device.

BRIEF DESCRIPTION OF THE DRAWINGS

Further objects, features, and advantages of the invention will become apparent from the following description of an example of the method according to the invention, as well as an embodiment of the loading device according to the present invention. Reference being made to the accompanying drawings, in which

FIGS. 18A,B to 20A,B are fragmentary perspective views and axial cross-sectional views, respectively, showing preferred embodiments of the loading tube delivery tip having improved security;

FIG. 22 corresponds FIG. 2 and is a side view illustrating in a detail drawing of the device of FIG. 21, wherein the bending member, the bushing and the tool are assembled;

FIG. 23 is a cross-sectional side view illustrating in a detail drawing an assembly comprising the bushing assembled on the tool, the bending member assembled thereon, the guide cover and a connecting element interconnecting the guide cover and the remaining elements displaceably via the bending element;

FIG. 24 is a cross-sectional side view illustrating in detail the an assembly comprising the guide cover and a connecting displaceable interconnecting element interconnecting the guide cover and the bending element of FIG. 23;

FIG. 25 is a cross-sectional side view showing the elements of FIG. 24 with the bending element slidingly displaced in relation to the guide cover, but still interconnected by the displaceable interconnecting element;

FIG. 26 is a cross-sectional side view showing the elements of FIG. 25 and the assembled bushing and tool, in the displaced position of FIG. 25;

FIG. 27 corresponds FIG. 3 and is a side view illustrating the device of FIG. 21, wherein the assembly of the bending member and the bushing is passed onto the tool, but an anchoring security string is not yet fixed to the tool;

FIG. 28 corresponds FIG. 4 and is a side view illustrating the loading device of FIG. 27, wherein the anchoring security string of the bushing now is anchored to the tool;

FIG. 29 corresponds FIG. 6 and is an axial cross-sectional view of the loading device of FIG. 21, wherein the assembly of FIG. 23 is attached to the central portion of the loading tube, and wherein the loading device of the embodiment is shown as a self-contained pre-use assembly;

FIG. 30 corresponds FIG. 7 and is an axial cross-sectional view of the loading device of FIG. 29, wherein the tool has been pushed towards the loading tube, illustrating the start of the automatic retainer bending process;

FIG. 31 is a cross sectional view illustrating in detail the start of the automatic retainer bending process of FIG. 30;

FIG. 32 corresponds FIG. 9 and is an enlarged cross-sectional view illustrating the retainer bending even more detailed;

FIG. 33 corresponds FIG. 10 and is a cross-sectional view, wherein the tool is pushed further into the loading tube, the bushing being released from the bending member, and the flanges being bent axially away from the ends of the bushing;

FIG. 34 corresponds FIG. 12 and is an axial cross-sectional view, wherein the tool is pushed further into the loading tube;

FIG. 35 corresponds FIG. 13 and is a side view of the loading device of FIG. 34;

FIG. 36 corresponds FIG. 14 and is a cross-sectional view, wherein the front end of the loading device of FIG. 34 is shown inserted into a flexible wall;

FIG. 37 is a cross-sectional view wherein the tool from FIG. 34 is pushed further into the loading tube and wherein the front flange of the bushing is pushed through the front end of the loading tube, the front flange being transversely unfolded;

FIG. 38 corresponds FIG. 15 and illustrates in addition to FIG. 37 the flexible wall in relation to the unfolded front flange;

FIG. 39 corresponds FIG. 16 and is an axial cross-sectional view, wherein the bushing is released from the loading tube and the rear flange is transversely unfolded on the other side of the wall; and FIG. 40 corresponds FIG. 17 and is an axial cross-sectional view, wherein the loading tube assembly is removed and only the tool is still attached to the bushing, before the safety string and the tool is removed and the bushing is finally inserted into the wall.

DESCRIPTION OF EMBODIMENTS

Figure 1:
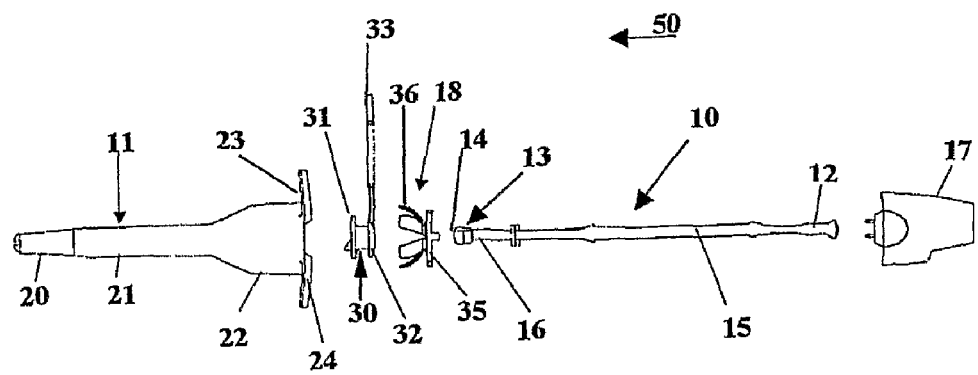
FIG. 1 is a side view illustrating the components of the loading device according to an embodiment of the invention, comprising a loading tube, a tool, a bushing having flanges, a bending member and a guide cover.

In FIG. 1 the components of a loading device according to a first embodiment for practising a method according to the invention are shown. The loading device is a tool for inserting a bushing 30 into a flexible wall, comprising an inserter 10 constructed as an elongate shank, a loading tube 11, a bending member 18, and a rear guiding cover 17, all of a plastics material or any other suitable material.

The loading tube 11 comprises an introduction section 22 narrowing in insertion direction 50 into an elongate delivery section 21 ending in a tip section 20. At the end opposite to tip 20, two gripping appliances 23, 24 are arranged transversally on the loading tube 11.

The inserter 10 has at one end thereof a handle 12 adapted to applying an axial force pushing the inserter into the loading tube 11, and at the other end a cylindrical head 13 including a conically bevelled end portion 14. Between the handle and the head the inserter forms adjacent the handle a flat portion 15 having a substantially rectangular cross-section, and adjacent the head a portion 16 having circular cross-section. In portion 15 there is provided adjacent portion 16 a key hole (not shown) forming a wider circular portion and a narrower slot-shaped portion for attaching an anchoring security string 33, as will be described below.

Delivery section 21 of loading tube 11 may have a cylindrical lumen but preferably the lumen thereof tapers conically from a larger inside diameter at the end of the loading tube adjacent to introduction section 22, the right end in the drawings, to a smaller inside diameter at the delivery end 20 of the loading tube 11, the left end in the drawings.

The bushing 30 that is to be inserted into the loading tube 11 and to be mounted in a flexible wall by the method according to the invention and by using the loading device described, is cylindrically tubular and forms a central passage. It has at each end a flange 31 and 32, respectively, integral with the rest of the bushing 30. The anchoring security string 33 is formed as a tail integral with flange 32. The flanges, including string 33, or the bushing in its entirety consists of an elastic material, e.g. rubber or rubberlike plastics. Inside the bushing 30 there may be provided some kind of mechanism, for instance a one-way valve 45, or the bushing may be constructed as a connection for connecting a hose or another conduit for gas or liquid. It is not necessary that the flanges are elastic; they can be more or less rigid and be provided with bending scores allowing the flanges to be folded, or they may comprise a number of foldable flaps, which may overlap at adjacent edges when being folded.

Bending member 18 comprises a rigid disk 35, a central axial passage for releasably receiving bushing 30, and wings 36. Disk 35 comprises radially arranged keying recesses 61 for ensuring the correct radial orientation of bushing 30 inside the delivery tool 1. The keying recesses 61 mate with protrusions 62 on the inside of introduction section 22 of loading tube 11. Bushing 30 is pushed into the central passage of bending member 18 into the position best seen in FIG. 2. Flanges 31, 32 are arranged on each side of disk 35 and the central cylindrical tube of bushing 30 is inserted into the central passage of bending member 18. Flange 31 rests against wing 36 and flange 32 rests against disk 35. In such a manner bushing 30 is removably kept in bending element 36 providing an assembly 37.

Assembly 37 is passed onto head 13, which is sized that it can be introduced into the central passage of the bushing until it engages an inside bulge 39 in the passage, providing an assembly 38. The head 13 is retained firmly, but not too tightly, in the passage by friction, such that head 13 may be released from bushing 30 by withdrawing inserter 10 opposite the direction of insertion 50, i.e. to the right in the drawings. Assembly 37 is now anchored to the inserter 10 in the manner disclosed in FIGS. 2 and 3.

Figure 4:
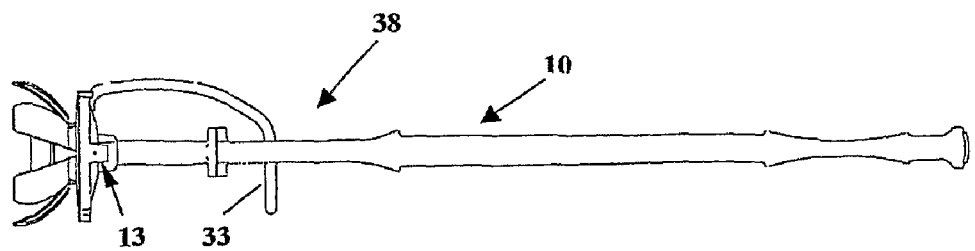
FIG. 4 is a side view illustrating the loading device of FIG. 3, wherein an anchoring security string of the bushing is anchored to the tool.

As illustrated in FIG. 4, improved security may be obtained by inserting anchoring string 33 at the end portion thereof into the above-mentioned key hole of inserter 10, and then pulling it firmly in the direction towards head 13 into the narrower portion of the key hole (not shown), whereby the string is clamped in said latter portion.

Figure 5:
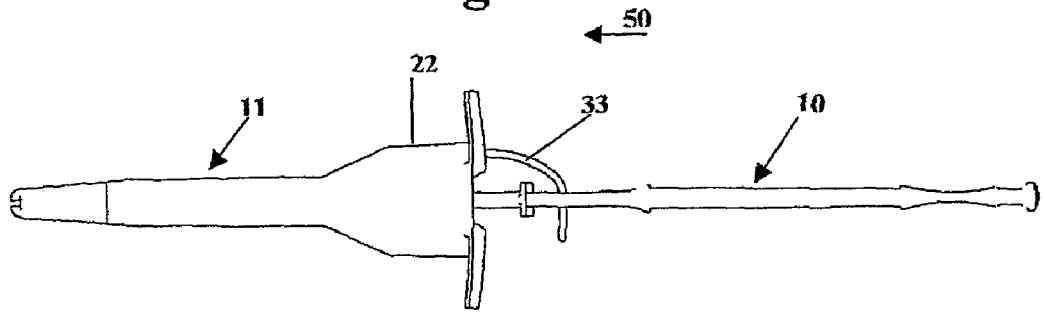
FIG. 5 is a side view illustrating the loading device of FIG. 4, wherein the tool with the bushing and the bending member is passed into the central portion of the loading tube.

In FIG. 5 it is shown that assembly 38 is manoeuvred in the direction of arrow 50 into the interior of loading tube 11 at introduction section 22. Thus housed inside loading tube 11, the guiding cover 17 is pushed over and passed along inserter 10 resulting in the self-contained assembly 55 illustrated in FIG. 6.

Guiding cover 17 comprises a central axial passage for slideably receiving inserter 10. Guiding cover 17 fullfils a number of purposes. Firstly inserter 10 is provided with a guiding support in the central passage of guiding cover 17 in such a manner that the inserter 10 can move longitudinally within the loading device. This improves the precision of loading and mounting bushing 30 into the loading tube 11 and further into a flexible wall 60, as will be discussed below. Secondly, the length of guiding cover 17 is adapted to the length of inserter 10. Furthermore, the guiding cover 17 provides a tangible feedback to the user about the position of bushing 17 in relation to the loading device, as will be described further below. Moreover, the guiding cover 17 provides a protection of the inside of the loading device against the outer environment. Thus, guiding cover 17 avoids for instance that contaminants reach bushing 30 or that bushing 30 is mechanically affected, for instance during transport, which would render the result of loading bushing 30 into wall 60 unreliable.

Figure 6:
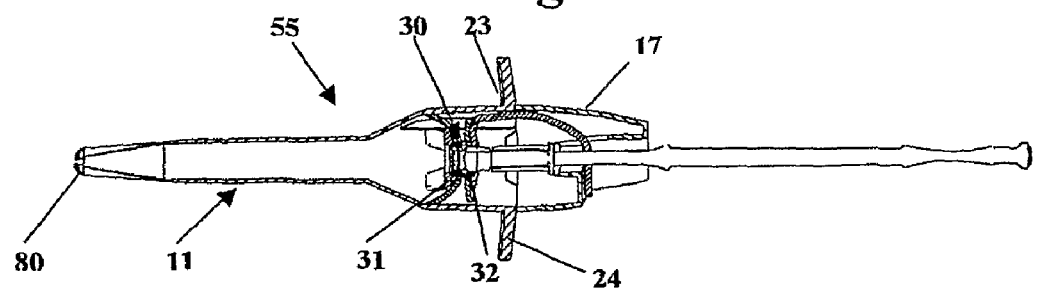
FIG. 6 is an axial cross-sectional view of the loading device of FIG. 5, wherein a guiding and closing cover is passed over the tool and fixed to the central portion of the loading tube, and wherein the loading device of the embodiment is shown as a self-contained pre-use assembly.

When assembled, as shown in FIG. 6, the loading device constitutes a self-containing loading device, pre-loaded with a bushing 30, ready for use, i.e. for inserting the bushing in a flexible wall. FIGS. 1-6 illustrate the manufacturing process of such a self-contained assembly 55, conveniently ready for use without the need of further preparation work concerning the loading device. Assembly 55 may be packaged appropriately, e.g. in a sterile or dust-free environment, and hence be conveniently transported and stored prior to use.

With reference to FIGS. 7-17, a convenient and secure method of mounting bushing 30 in a flexible wall 60 by means of the embodied loading device is illustrated. For inserting bushing 30 into the flexible wall 60, the loading device is preferably hold by an operator in the following convenient one-hand syringe-like grip. The operator's index finger and middle finger of the same hand are engaged with handle 23 and 24, respectively. More precisely, the tip of the fingers are against the insertion direction 50 placed on the surface of handles 23, 24 that is pointing towards the tip 80 of the loading device. Furthermore, the operators thumb of the same hand is placed in insertion direction on end 19 of inserter 10. Thus, the loading device is conventionally hold by one hand and the insertion of bushing 30 into wall 60 is performed with one hand by pushing it in insertion direction 50 with inserter 10. This conveniently frees the other hand of the operator for tasks performed simultaneously. Moreover, the syringe-like grip is well-known, even to less medically trained operators, and the handling of the loading device is rendered virtually self-explaining.

Figure 7:
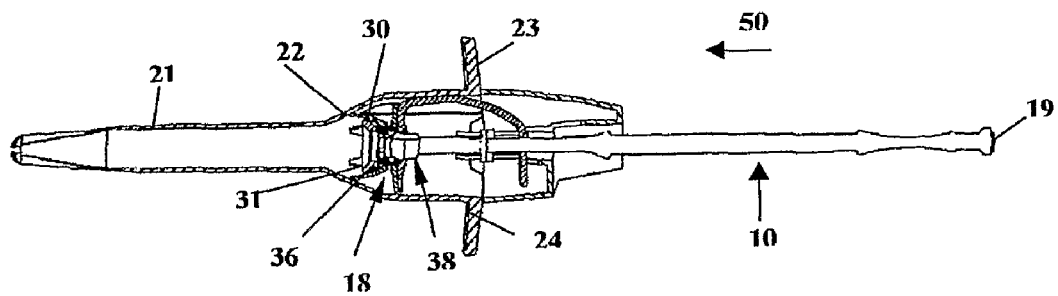
FIG. 7 is an axial cross-sectional view of the loading device of FIG. 6, wherein the tool has been pushed towards the loading tube, illustrating the start of the automatic retainer bending process.
Figure 8:
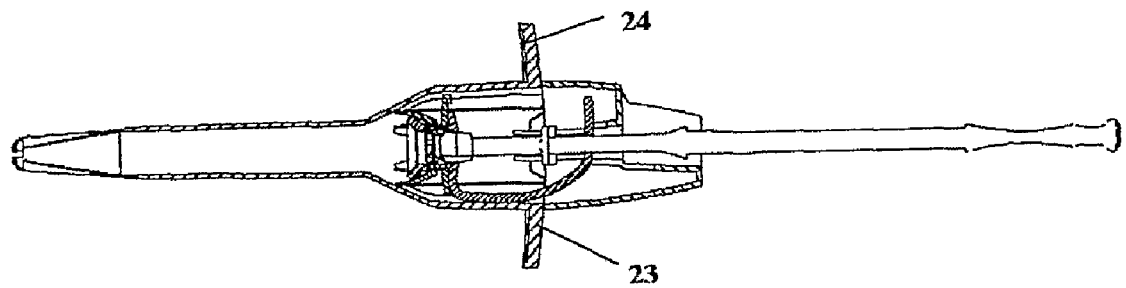
FIG. 8 is an axial cross-sectional view of the loading device of FIG. 6, wherein the loading device has been rotated axially 180 degrees, i.e. the anchoring security string is now oriented downwards.
Figure 9:
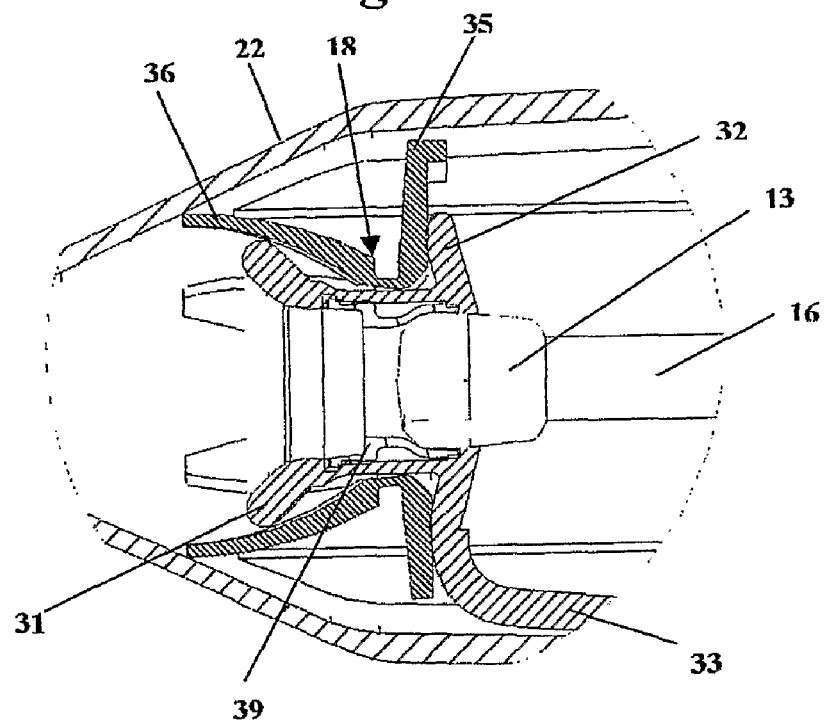
FIG. 9 is an enlarged cross-sectional view illustrating the retainer bending more detailed.
Figure 10:
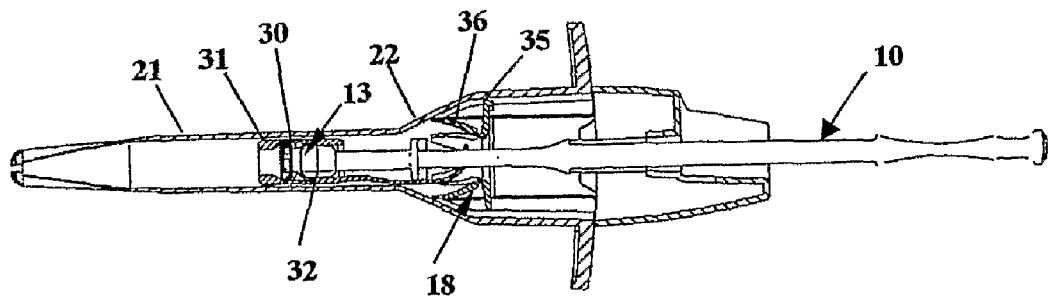
FIG. 10 is a cross-sectional view, wherein the tool is pushed further into the loading tube, the bushing being released from the bending member, and the flanges being bent axially away from the ends of the bushing.

In FIG. 6 the beginning of a sequence of bending flanges 31, 32 of bushing 30 initially oriented radially away from the main cylindrical body of bushing 30 is shown. In FIG. 7 assembly 38 comprising the bending member 18, which during the above assembly of the loading device has received bushing 30 in its central passage, is pushed forward in insertion direction 50 by pushing inserter 10 in said direction. This forward movement causes wings 36 of bending member 18 at first to abut against the radially inclined interior wall of the introduction section 22 of the loading tube 11. Wings 36 are moveable, substantially in radial direction towards the central longitudinal axis 90 of the loading device, e.g. shown in FIG. 13. By further pushing assembly 38 forward in direction 50, the wings of bending member 18 are forced to move radially inward. This results consequently in a longitudinally forward and radially inward movement of flange 31, forwarding it into elongate loading tube segment 21, as depicted in FIGS. 9 and 10. By pushing inserter 10 further in insertion direction 50, the rigid disk 35 of bending member 18 abuts against the interior wall of inclined section 22, thus stopping further displacement of bending member 18 in insertion direction 50. When inserter 10 is pushed even further in insertion direction 50, an increasing pushing force results in bushing 30 being pushed off the central passage of bending member 18. Bushing 30 is thus released from the central passage of bending member 18 and free for a subsequent forwarding into loading tube 11. Upon further displacement of tool 10, bushing 30 moves on in insertion direction 50, still attached to head 13, and thus together with tool 10. Flange 32 slips through the central passage of bending member 18 and is bent axially backward, as seen in inserting direction 50.

Hence, flanges 31 and 32 are automatically bent into the shown orientations. There is no need for manually squeezing, pushing, folding, or for performing similar mechanical tasks on one of the flanges 31, 32 in order to achieve the orientation as shown in FIG. 10.

For facilitating displacement of the bushing 30 along the loading tube 11, the latter may be pre-lubricated internally or coated with a suitable material on the interior surface thereof.

Figure 14:
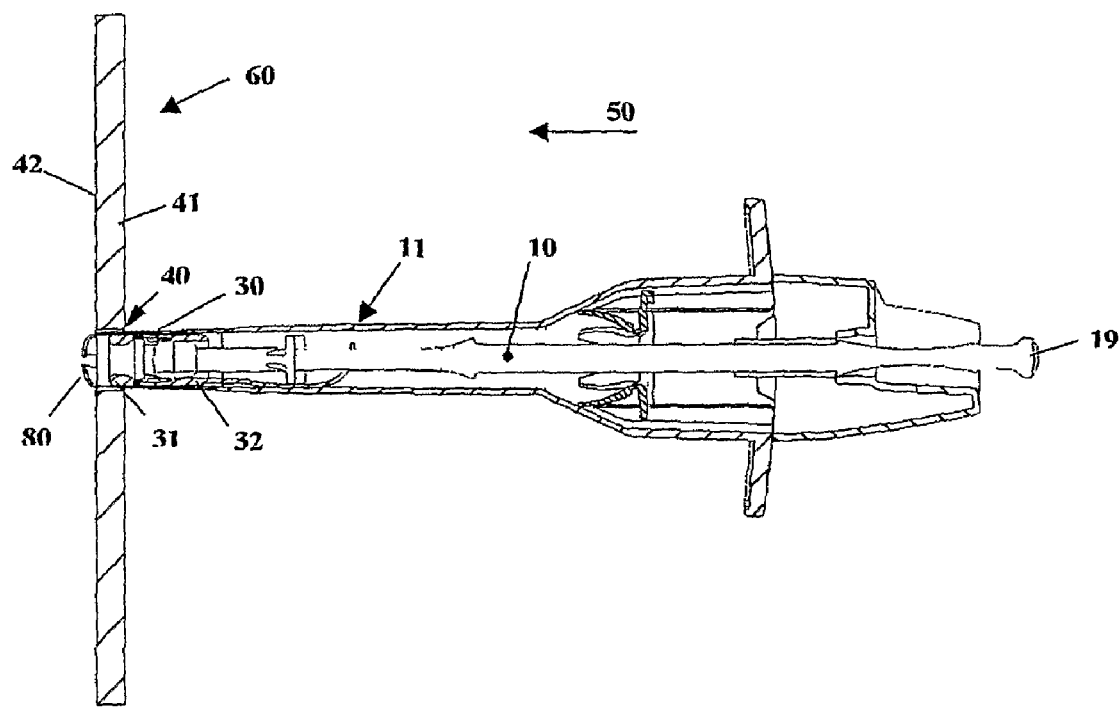
FIG. 14 is a cross-sectional view, wherein the front end of the loading device of FIG. 12 is shown inserted into a flexible wall.

In order to introduce the bushing into an aperture 40 in a flexible wall 60, which is accessible from one side 41 but not from the other side 42, the inserter 10 with the loading tube 11 and the bushing 30 is now pushed with tip 80 and as a unit through aperture 40 from wall side 41 in insertion direction 50, i.e. towards the left in the figures, resulting in the position as illustrated in FIG. 14. Alternatively, the tip 80 of the loading device is inserted into aperture 40 prior to pushing forward inserter 10 from the position as shown in FIG. 6, and subsequently the above steps are performed arriving at the state illustrated in FIG. 14. By further pushing on end 19 of inserter 10 inserter 10 moves further in insertion direction, resulting in the position shown in FIG. 15.

In the following step, illustrated in FIG. 15, the inserter 10 and the bushing 30 are pushed forward in the loading tube 11, which is held stationary by the operator, so that flange 31 will be located outside the tip 80 of the loading tube 11. This position of the loading tube in relation to the inserter 10 is indicated to the operator at the back end of the loading device at guiding cover 17. There, the end 19 of inserter 10 is in register with the top of guiding cover 17, as illustrated on the right of FIG. 15. Thus, flange 31 is allowed to be unfolded on side 42 of wall 60. When this has taken place, the loading device with the loading tube and the bushing is withdrawn as a unit towards the right opposite to insertion direction 50, until flange 31 engages wall side 42. The pull applied to the loading device possibly being so great that wall 60 will be partly compressed. Due to anchoring by means of the anchoring security string 33 and also to some extent due to friction between the bushing and the head 13, if any, the bushing is prevented from sliding off the inserter 10. With the flange 31 thus engaged with the wall side 42 of the wall 60, the loading device is further withdrawn over inserter 10 in order to release also flange 32, so that it unfolds on the opposite wall side 41 of the flexible wall 60, as illustrated in FIG. 16.

Subsequently, the loading tube 11 is withdrawn completely from the inserter 10, see FIG. 17. Then, anchoring string 33 is disconnected from inserter 10, which is withdrawn from the bushing 30, which will then be left in wall 60 with the flanges 31, 32 projecting around the aperture 40 at opposite sides 31, 32 of the wall 60. Due to the flexible wall 60 being compressed between the flanges 31, 32 of bushing 30, a tight and stable attachment of the bushing 30 in the wall 60 will be secured. String 33 is cut off, and mounting of the bushing 30 in the aperture 40 is completed.

Figure 11:
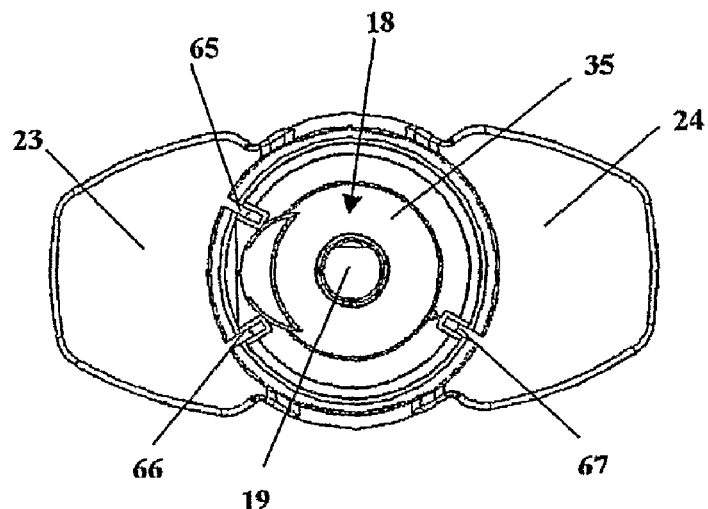
FIG. 11 is an end view of the loading device of the previous Figures as seen axially in insertion direction.

FIG. 11 shows in an end view in axial direction another security feature of the loading device, wherein guiding cover 17 is removed for illustrative purposes. Disk 35 comprises radially arranged keying elements 65, 66, 67 for ensuring the correct front/rear-orientation of bending member 18 in relation to the loading device. This orientation is ensured by means of keying elements 65, 66, 67 mating with protrusions inside the rear guiding cover 17 and with protrusions 62 on the inside of introduction section 22 of loading tube 11. Thus, the disk 35 fits only in one orientation inside cover 17 and loading tube 11. Bending member 18 consequently may only be housed inside the delivery device with the wings 36 oriented forwardly into the direction of the loading tube 11.

The inserter 10 must of course be adapted to the bushing 30 to be mounted in the flexible wall 60, which can have varying appearance and dimensions depending on the purpose for which it is intended but shall always include a tubular element with flanges at the ends. It is not necessary that the element terminates at the flanges; it can also project beyond one or the other of the flanges. The flanges should be resilient in order to be folded and then, when they are released, to return to their normal shape, and in case also the tubular element is of an elastic material the element and the flanges can be made integral. Possibly, the element in that case may be provided with a stiffening insert in the central passage thereof.

In order to facilitate the insertion of loading tube 11 through aperture 40 in wall 60, even if the loading tube should be directed not perpendicularly but to some extent obliquely to wall surface 41, the loading tube preferably is shaped in the manner disclosed in the drawings at the end 20 thereof, i.e. the narrower left end in the drawing. As can be seen e.g. in FIG. 1, the tube end 20 is slotted to form a number of inwardly curved flaps. In this case, the material of the tube should be sufficiently flexible so that the flaps are sufficiently yieldable in order to allow bushing 30 to be pushed out from the loading tube end 20. By the curved shape of the flaps, the loading tube has no sharp edge that may engage the edge of aperture 40 at the insertion. On the contrary, the loading tube end will be gently guided into the aperture by means of the cupola-shaped end formed by the curved flaps.

When displacing bushing 30 through this type of expanding tip 80 of loading tube 11, it is desired that the maximum diameter achieved does not exceed the diameter of aperture 40. This is important in cases where the aperture material might be damaged by pressure exerted on it by tip 80, when inserted into the aperture, or where the diameter of aperture 40 might be enlarged by such action, which would result in a too loose positioning of bushing 30 in aperture 40.

To solve this problem, FIGS. 18A,B to 20A,B show fragmentary perspective views and axial cross-sectional views, respectively, of preferred embodiments of the loading tube delivery tip providing improved security. In the embodiments of end portion 20 illustrated in FIGS. 18A,B to 20A,B loading tube 11 consists of an elastic material and tapers towards the opening on the outside of said end portion in order to facilitate the insertion of the loading tube into aperture 40. After such insertion the bushing 30 can be pushed out of the loading tube end portion 20 thereof, being expanded under resilient yielding when the bushing 30 is passing through the end portion 20. Furthermore, the end portions 100, 101, 102, being exemplary embodiments of end portion 20, comprise limiting means 110, 120, 131 for limiting the radially outward movement of flaps 111, 121, 130 respectively. Limiting means 110, 120, 131 limit said radially outward movement, such that the outside diameter of end portions 100, 101, 102 do not substantially exceed the inner diameter of aperture 40.

More precisely, limiting means 110, shown in FIGS. 18A, B, is a thin hose of a resilient material passed circumferentially over flaps 111 and over a certain distance of the unslotted portion of tip 100. Hose 110 is attached to tip 100 either by frictional force or by other suitable means, e.g. glueing or hotwelding. Hose 100 limits the radial outward movement of flaps 111 due to the increasing resilient force with increasing radial distance from the longitudinal axis of the loading device. Moreover, hose 100 supports the resilient movement back to the position shown in FIGS. 18A,B, once bushing 30 is pushed out of tip 100 and inserted into wall 60. Similarly, tip 101 of loading tube 11 shown in FIG. 19A and FIG. 19B has a hose passed on flaps 121. However, hose 122 has not necessarily to be made of resilient material, it is sufficient that the material of hose 120 is flexible. As can be seen in the drawing, hose 120 forms folds 122 extending radially inward into the spaces in-between flaps 121. When flaps 121 are pushed radially outward by bushing 30 being pushed out of tip 101, foldings 122 unfold and limit further radial outward movement of flaps 121 when fully unfolded. Another alternative of a limiting means is shown in FIGS. 20A,B, wherein folds 131 are an integral part of flaps 130, the folds being manufactured together with the flaps e.g. by the same extrusion process.

Now turning to FIGS. 21-40, a further embodiment of the present invention is elucidated. FIGS. 21-40 describe an alternative embodiment of the device according to the invention, its manufacturing method and a method for insertion.

Figure 21:
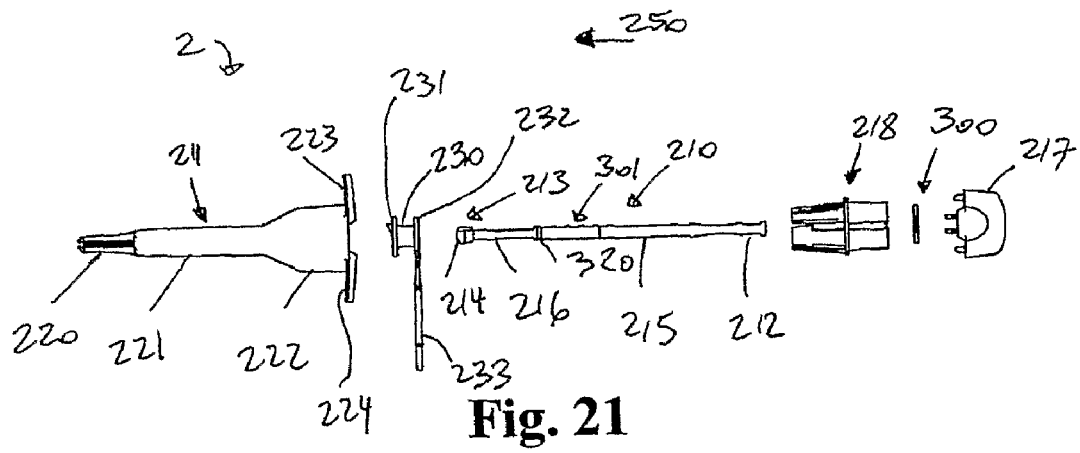
FIGS. 21-40 describe an alternative embodiment of the device according to the invention, wherein FIG. 21 corresponds FIG. 1 and is a side view illustrating the components of the loading device according to a further embodiment of the invention, comprising a loading tube, a tool, a bushing having flanges, a bending member, a displaceable interconnecting element, and a guide cover.

FIG. 21 corresponds FIG. 1 and is a side view illustrating the components of the alternative loading device, namely a loading tube, a tool, a bushing having flanges, a bending member, a displaceable interconnecting element, and a guide cover. More precisely, the components of a further loading device for practising a method according to the invention are shown. The loading device is a tool for inserting a bushing 230 into a flexible wall, comprising an inserter 210 constructed as an elongate shank, a loading tube 211, a bending member 218, an interconnecting element 300 and a rear guiding cover 217, all of a plastics material or any other suitable material.

The loading tube 211 comprises an introduction section 222 narrowing in insertion direction 250 into an elongate delivery section 221 ending in a tip section 220. At the end opposite to tip 220, two gripping appliances 223, 224 are arranged transversally on the loading tube 211.

The inserter 210 has at one end thereof a handle 212 adapted to applying an axial force pushing the inserter into the loading tube 211, and at the other end a cylindrical head 13 including a conically bevelled end portion 214. Between the handle and the head the inserter forms adjacent the handle a flat portion 215 having a substantially rectangular cross-section, and adjacent the head a portion 216 having circular cross-section. In portion 215 there is provided adjacent portion 216 a key hole (not shown) forming a wider circular portion and a narrower slot-shaped portion for attaching an anchoring security string 233, as will be described below, as well as a portion 301 for attaching the end of security string 233 to inserter 210 so that any risk of occluding the loading tube 211 with the free end of the security string 233 is excluded. Portion 301 comprises e.g. a groove for this purpose, wherein the end of security string is clamped in the groove. Portion 301 of the self-contained device described herein is prior to use outside of cover 217, so that it easily is occularly inspected and confirmed that security string 233 is fixed to tool 210 in the portion 301. This further improves security of the device. Delivery section 221 of loading tube 211 may have a cylindrical lumen having a diameter adapted to receive bushing 230 in the folded position as will be described below.

The bushing 230 that is to be inserted into the loading tube 211 and to be mounted in a flexible wall by the method according to the invention and by using the loading device described, is similar to bushing 30 described above, i.e. it is cylindrically tubular and forms a central passage. It has at each end a flange 231 and 232, respectively, integral with the rest of the bushing 230. The anchoring security string 233 is formed as a tail integral with flange 232. The flanges, including string 233, or the bushing may in its entirety consists of an elastic material, e.g. rubber or rubberlike plastics.

Figure 2:
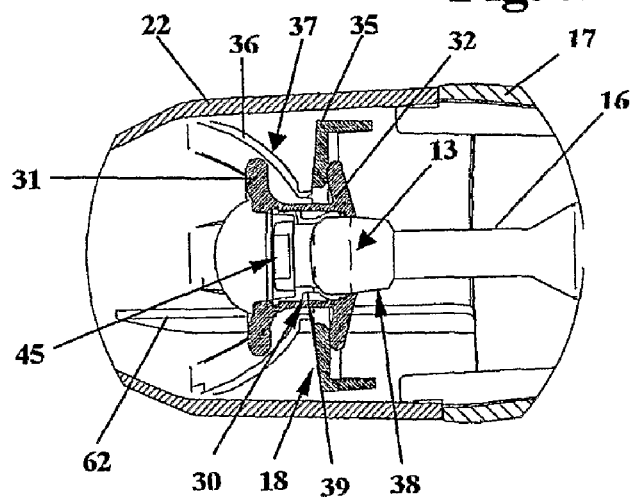
FIG. 2 is a side view illustrating in a detail drawing the device of FIG. 1, wherein the bending member, the bushing and the tool are assembled.
Figure 2:
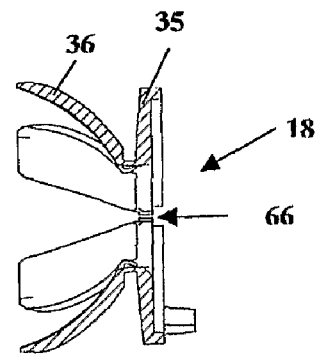
Figure 22:
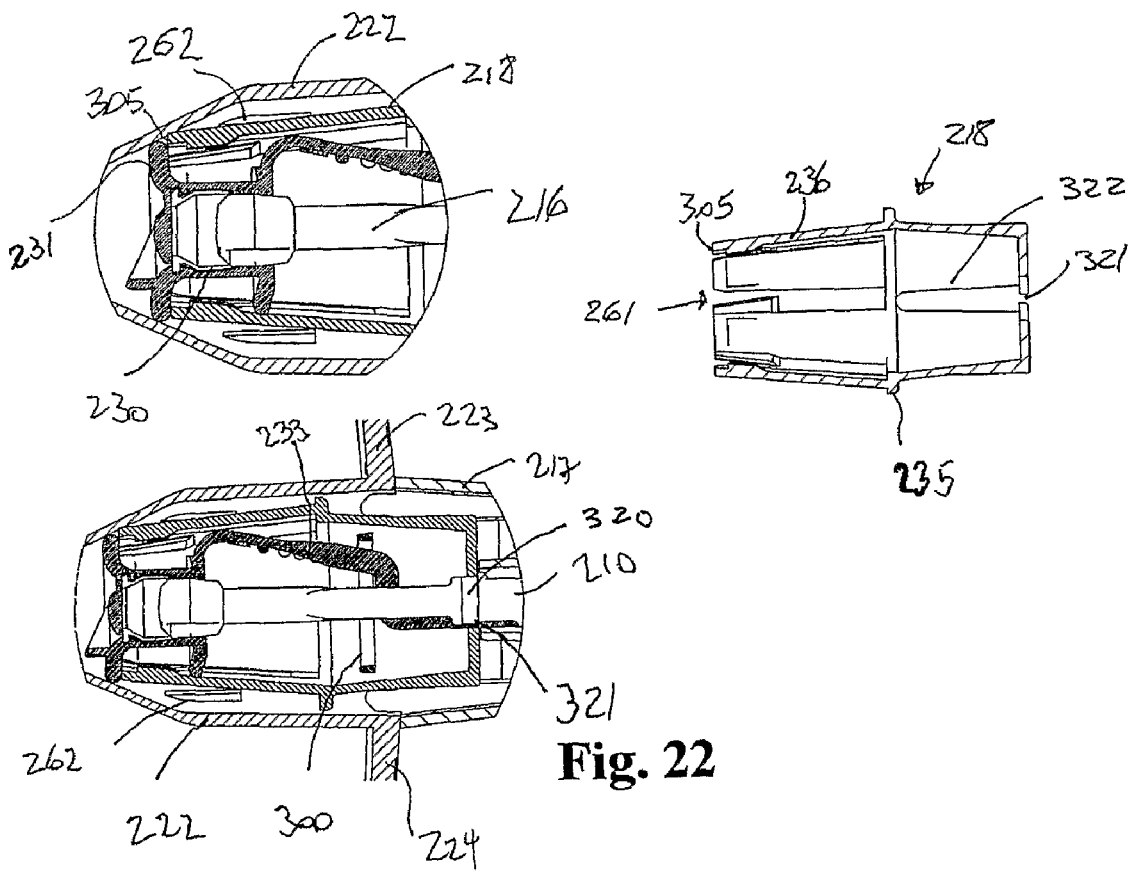

FIG. 22 corresponds FIG. 2 and is a side view illustrating in a detail drawing of the device of FIG. 21, wherein the bending member 218, the bushing 230, the interconnecting element 300 and the tool 210 are shown assembled on the left of FIG. 22. Bending member 218 is shown for itself on the right of FIG. 22.

Figure 23:
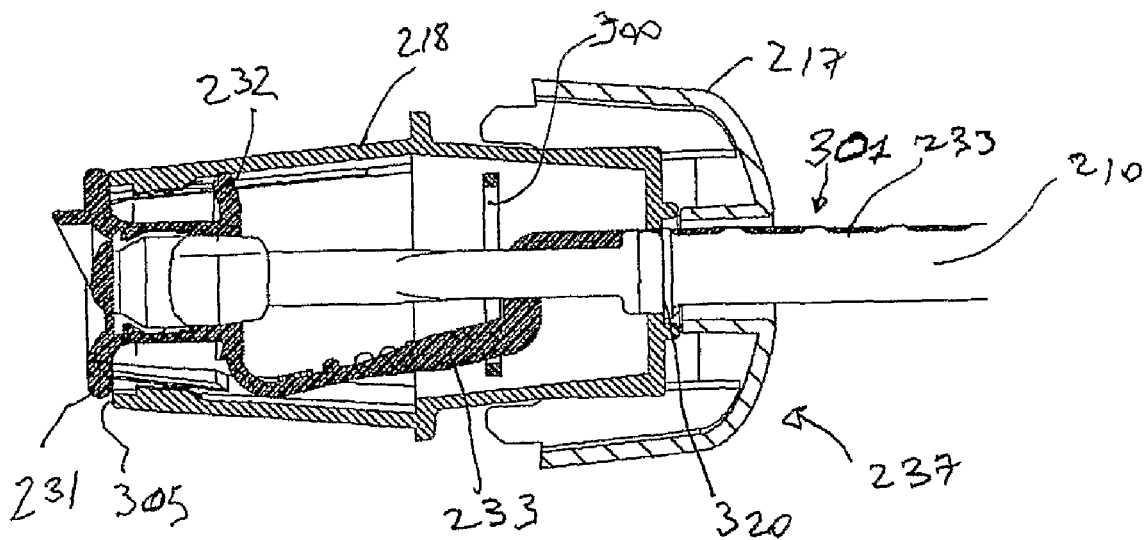

Bending member 218 comprises a ring 235, a central axial passage for releasably receiving bushing 230, and wings 236. Ring 235 does not comprise radially arranged keying recesses as disk 35, but instead recesses 261 between wings 236 ensure the correct radial orientation of bushing 230 inside the delivery tool 2. The "keying" recesses 261 mate with protrusions 262 on the inside of introduction section 222 of loading tube 211. Bushing 230 is pushed into the central passage of bending member 218 into the position best seen in FIG. 23 or 26. Flanges 231, 232 are arranged on one side of ring 235 and inside the central cylindrical tube of bushing 230 is inserted into the central passage of bending member 218. Flange 231 rests against wing 236, and more precisely against ends 305 of wings 236 as shown in the FIGS. Flange 32 rests inside bending member 218. In such a manner bushing 230 is removably kept in bending element 218 providing an assembly 237 of bushing, tool, bending member, interconnecting element and guiding cover. FIG. 23 is a cross-sectional side view illustrating in a detail drawing an assembly comprising the bushing assembled on the tool, the bending member assembled thereon, the guide cover and a connecting displaceable element interconnecting the guide cover and the remaining elements via the bending element.

Figure 26:
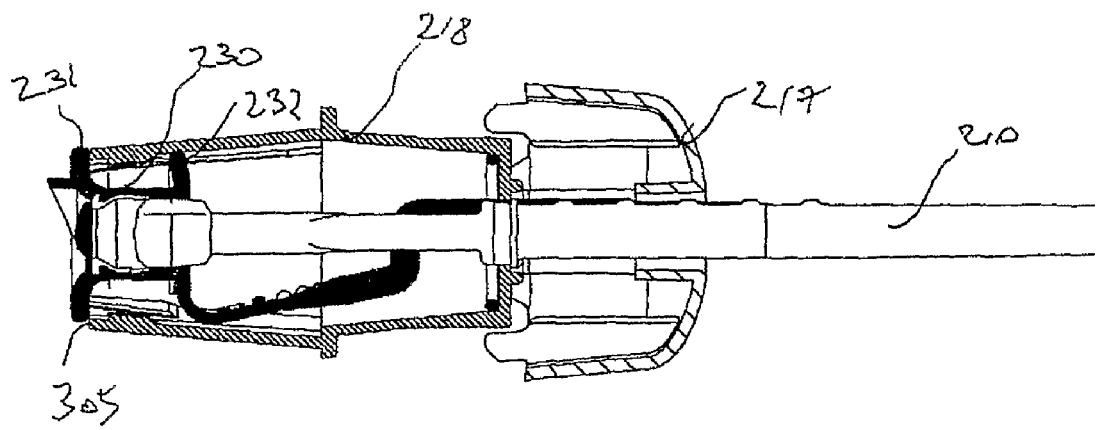

As can be seen in FIG. 23, the bending element 218 comprises a longitudinal slot with varying opening width for receiving interconnecting element 300. The varying opening width ensures that element 300 is varying an opening 321 of bending element 318 for receiving a locking element of tool 210 releasably. More precisely this means that the releasing force of tool 210 when pushed into direction 250 varies, i.e. decreases the further it is pushed in direction 250. Furthermore, the force to assemble tool 210 with bending element 210, as shown in the pulled out position with reference to guide 217, is rather low, thus facilitating assembly thereof. When retracting bending element 218 into the position shown in FIG. 23 or 24, the tool 210 is clamped with more force to the bending device, thus ensuring a stronger assembly. This ensures that tool 210 and element 230 does not accidentally release from bending device 218. Furthermore, this enables an easy re-insertion/re-assembly/re-loading of device 2 in case a qualified user has mishandled the device and regards it necessary to re-load the tool 210 with element 230 into the device. The user simply pulls tool 210 completely out of end 280, opens cover 217, inserts tool 210 easily into bending device 218 and cover 217 as shown in FIG. 26 are draws it back to a position as shown in FIG. 23, in order to lock tool 210 in this relative position, and then the assembly achieved is re-inserted into tube 210 in order to again result in a self-contained device 255. Also, a click sound indicates correct insertion when tool 210 is inserted into opening 321 with portion 321. Still, the securing string is securely in position in the groove at portion 301. This provides an advantageous reliability and security of the device.

More precisely, assembly 237 is achieved by passing bushing 230 onto head 213, which is sized that it can be introduced into the central passage of the bushing until it engages an inside bulge in the passage, providing a first assembly. The head 213 is retained firmly, but not too tightly, in the passage by friction, such that head 213 may be released from bushing 230 by withdrawing inserter 10 opposite the direction of insertion 250, i.e. to the right in the drawings. Assembly 237 is now anchored to the inserter 210 and inserted into bending member 218 in the manner disclosed in FIGS. 27.

Figure 28:
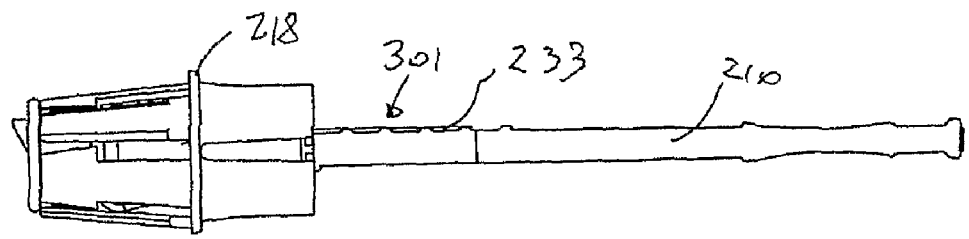

As for instance illustrated in FIG. 28, improved security may be obtained by inserting anchoring string 233 at the end portion thereof into the above-mentioned key hole of inserter 210, and then pulling it firmly in the direction towards head 213 into the narrower portion of the key hole (not shown), whereby the string is clamped in said latter portion. Further, the end is pushed into portion 301, so that it is perfectly integrated with tool 210 and not protruding from tool 210. Thus, any problems with securing string 233 occluding the loading tube are avoided.

Figure 24:
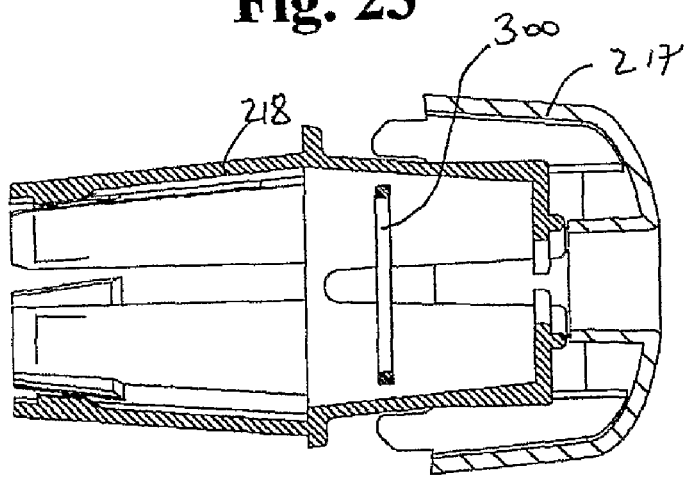

FIG. 24 is a cross-sectional side view illustrating in detail the an assembly comprising the guide-cover and a connecting interconnecting element interconnecting the guide cover and the bending element of FIG. 23, so that the bending element I displaceable in relation to the cover.

Figure 25:
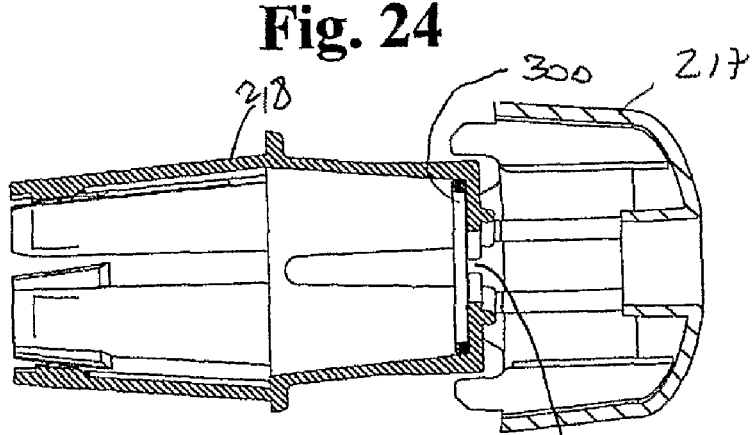

FIG. 25 is a cross-sectional side view showing the elements of FIG. 24 with the bending element slidingly displaced in relation to the guide cover, but still interconnected by the interconnecting element. In this position, tool 210 with bushing 230 assembled thereon is easily inserted into bending element 218, which itself is interconnected with guiding cover 217.

FIG. 26 is a cross-sectional side view showing the elements of FIG. 25 and the assembled bushing and tool, in the displaced position of FIG. 25.

Figure 3:
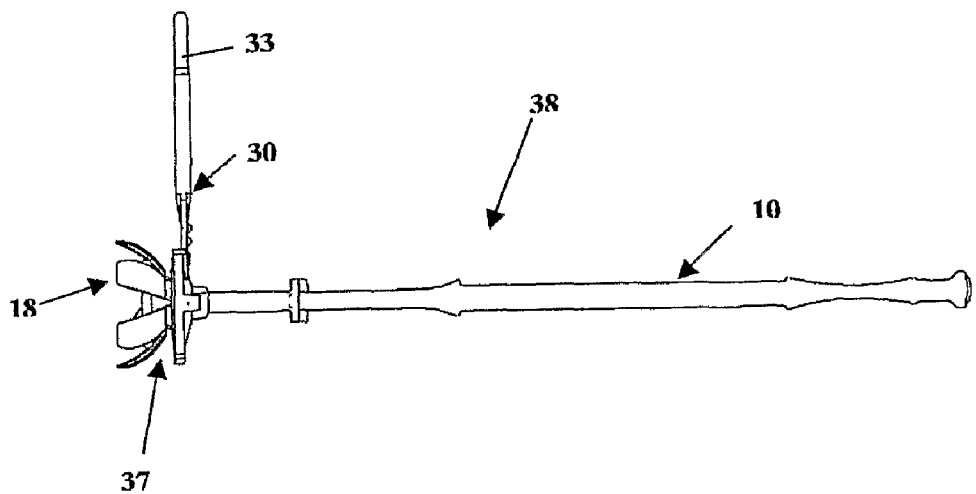
FIG. 3 is a side view illustrating the device of FIG. 1, wherein the assembly of the bending member and the bushing is passed onto the tool.
Figure 27:
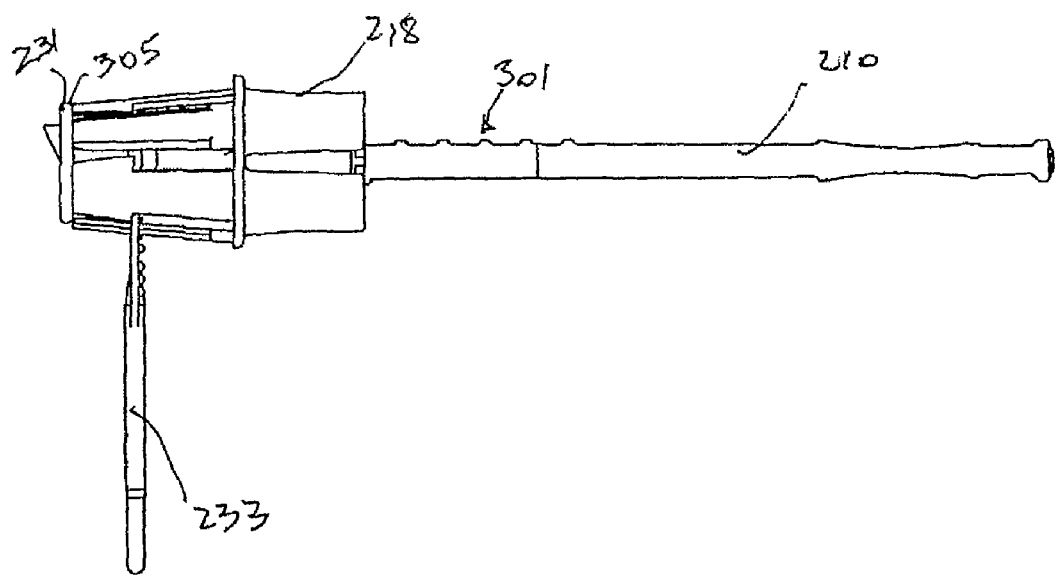

FIG. 27 corresponds FIG. 3 and is a side view illustrating the device of FIG. 21, wherein the assembly of the bending member and the bushing is passed onto the tool, but anchoring security string 233 is not yet fixed to the too.

FIG. 28 corresponds FIG. 4 and is a side view illustrating the loading device of FIG. 27, wherein the anchoring security string 233 of the bushing now is anchored to the tool 210.

Figure 29:
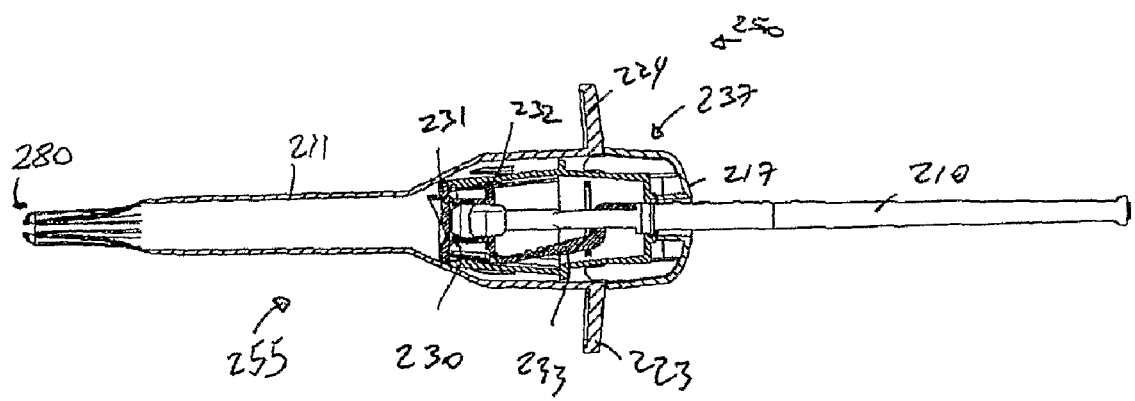

FIG. 29 corresponds FIG. 6 and is an axial cross-sectional view of the loading device of FIG. 21, wherein the assembly of FIG. 23 is attached to the central portion of the loading tube, and wherein the loading device of the embodiment is shown as a self-contained pre-use assembly;

In FIG. 29 it is shown that assembly 237 is manoeuvred in the direction of arrow 250 into the interior of loading tube 211 at introduction section 222. Thus housed inside loading tube 211, the assembly 237 is connected to loading tube 211. Thus, tool 2 is provided as a self-contained unit. There is not need to push guiding cover 217 is pushed over and passed along inserter 210 resulting in this step, as this has already been done in the previous assembly step. The self-contained assembly 255 illustrated in FIG. 29.

Guiding cover 217 comprises a central axial passage for slideably receiving inserter 210. Guiding cover 217 fullfils a number of purposes similarly as cover 17 described above.

When assembled, as shown in FIG. 29, the loading device constitutes a self-containing loading device, pre-loaded with a bushing 230, ready for use, i.e. for inserting the bushing into a flexible wall. FIGS. 21-29 illustrate the manufacturing process of such a self-contained assembly 255, conveniently ready for use without the need of further preparation work concerning the loading device. Assembly 255 may be packaged appropriately, e.g. in a sterile or dust-free environment, and hence be conveniently transported and stored prior to use.

With reference to FIGS. 30-40, a convenient and secure method of mounting bushing 230 in a flexible wall 260 by means of the embodied loading device is illustrated. For inserting bushing 230 into the flexible wall 260, the loading device is preferably hold by an operator in the following convenient one-hand syringe-like grip. The operator's index finger and middle finger of the same hand are engaged with handle 223 and 224, respectively. More precisely, the tip of the fingers are against the insertion direction 250 placed on the surface of handles 223, 224 that is pointing towards the tip 280 of the loading device. Furthermore, the operators thumb of the same hand is placed in insertion direction on end 219 of inserter 210. Thus, the loading device is conventionally hold by one hand and the insertion of bushing 230 into wall 260 is performed with one hand by pushing it in insertion direction 250 with device 2. This conveniently frees the other hand of the operator for tasks performed simultaneously. Moreover, the syringe-like grip is well-known, even to less medically trained operators, and the handling of the loading device is rendered virtually self-explaining. For further security the end 219, as well as handles 223, 224, may be ribbed for better grip.

Figure 30:
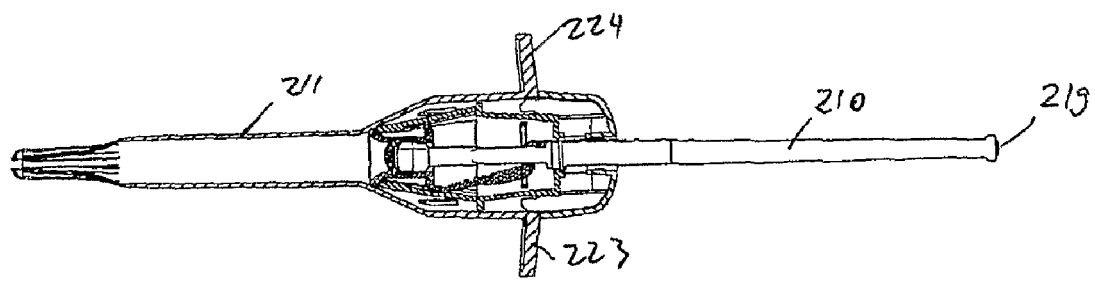

FIG. 30 corresponds FIG. 7 and is an axial cross-sectional view of the loading device 2 of FIG. 29, wherein the tool 210 has been pushed towards the loading tube 211, illustrating the start of the automatic retainer bending process.

Figure 31:
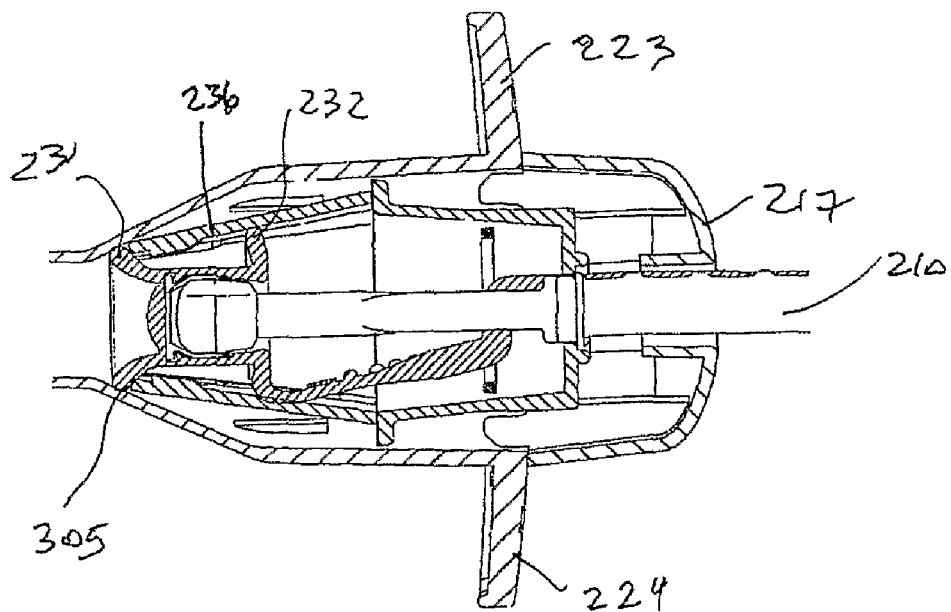

FIG. 31 is a cross sectional view illustrating in detail the start of the automatic retainer bending process of FIG. 30.

Figure 32:
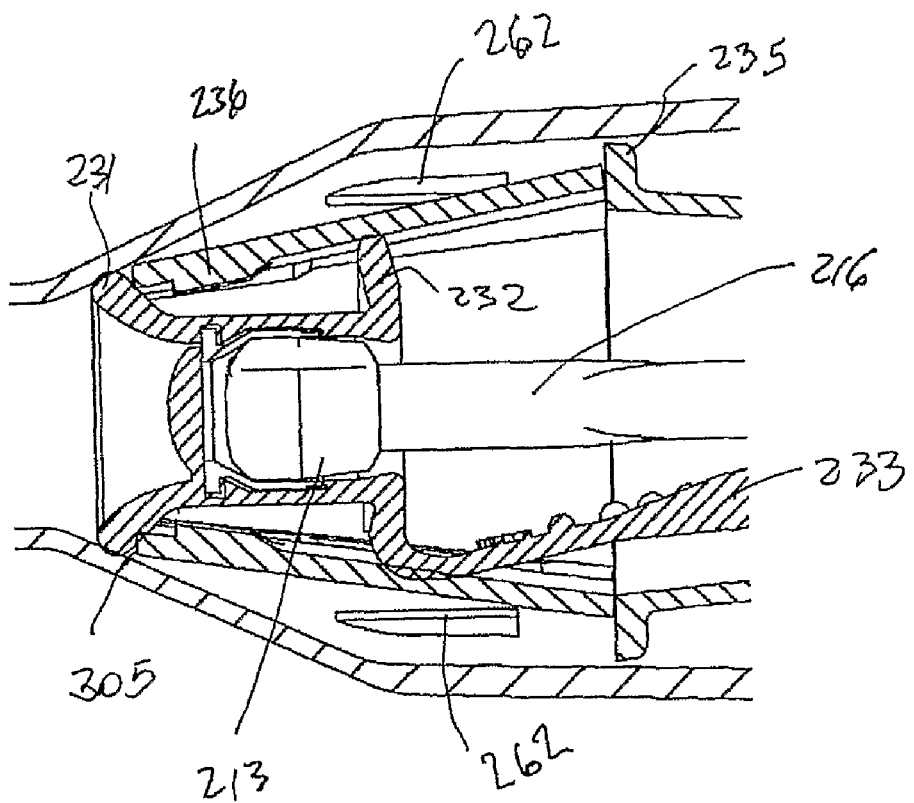

FIG. 32 corresponds FIG. 9 and is an enlarged cross-sectional view illustrating the retainer bending even more detailed.

Figure 33:
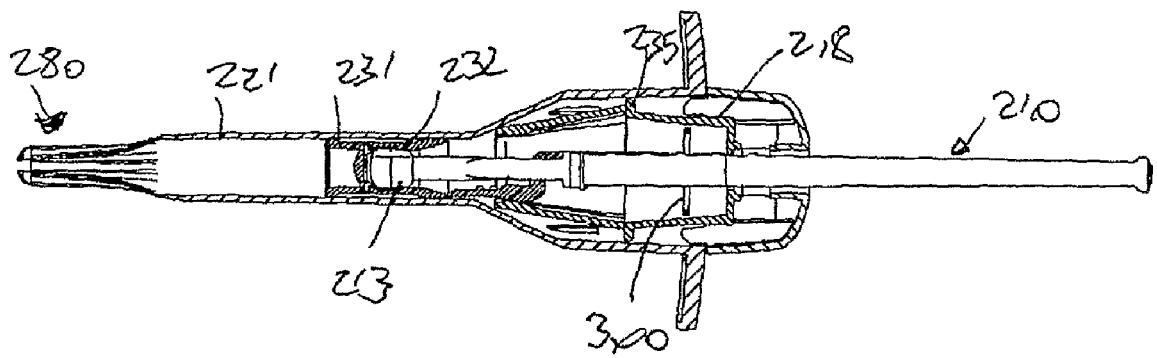

FIG. 33 corresponds FIG. 10 and is a cross-sectional view, wherein the tool 210 is pushed further into the loading tube 211, the bushing being 230 released from the bending member 218, and the flanges being bent axially away from the ends of the bushing.

Figure 12:
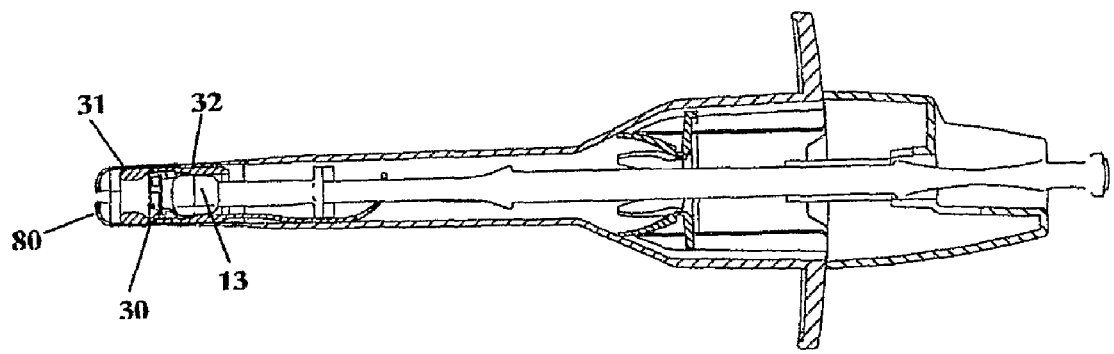
FIG. 12 is an axial cross-sectional view, wherein the tool is pushed further into the loading tube.
Figure 34:
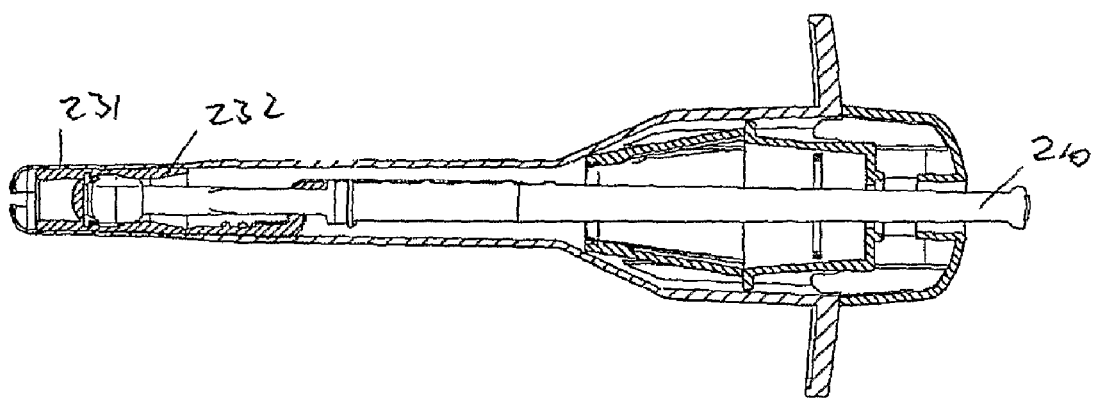

FIG. 34 corresponds FIG. 12 and is an axial cross-sectional view, wherein the tool 210 is pushed further into the loading tube 211.

Figure 13:
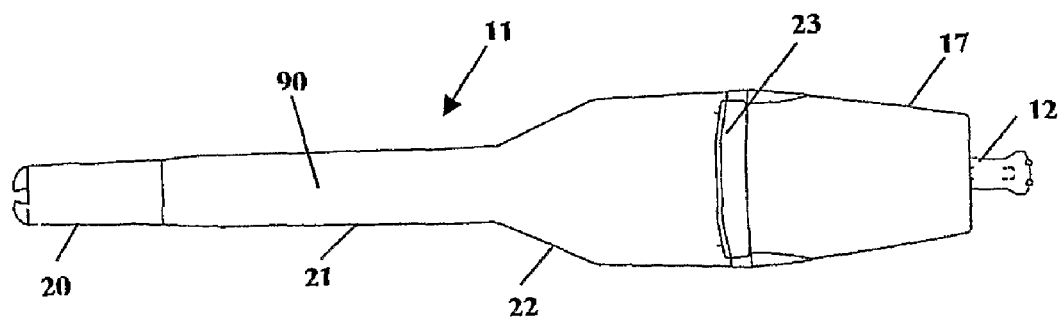
FIG. 13 is a side view of the loading device of FIG. 12 showing the orientation of the cross-sectional views of the loading device along the dot-and-dash line.
Figure 35:
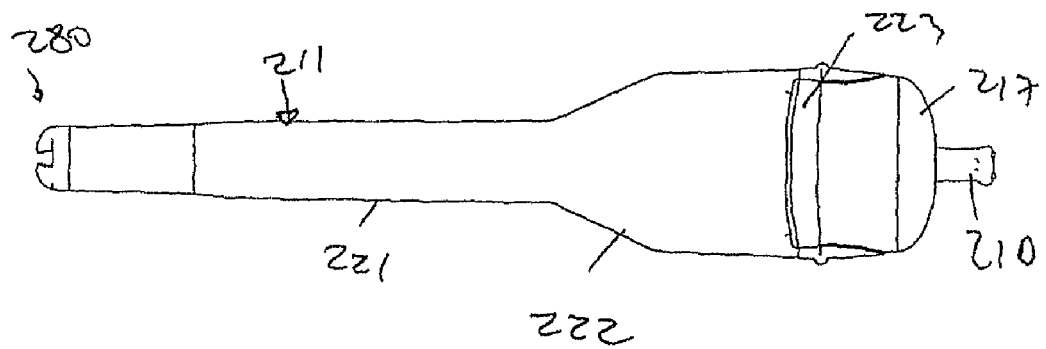

FIG. 35 corresponds FIG. 13 and is a side view of the loading device 2 of FIG. 34.

Figure 36:
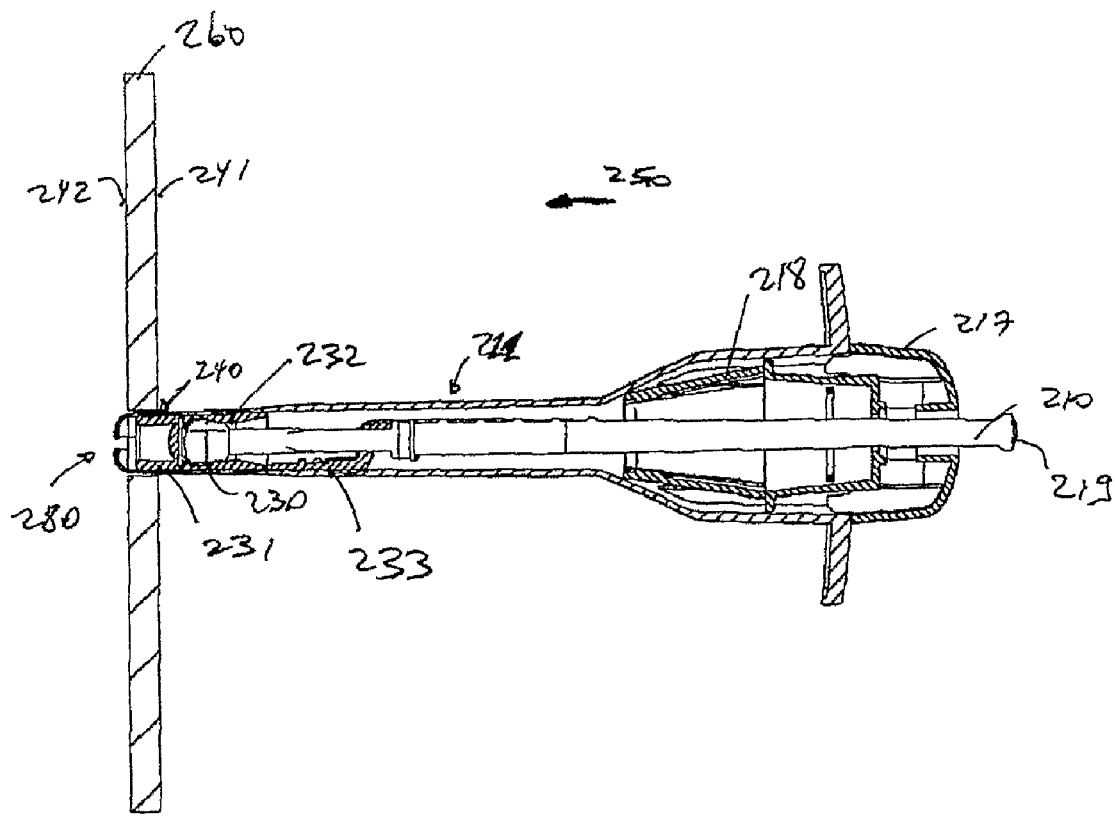

FIG. 36 corresponds FIG. 14 and is a cross-sectional view, wherein the front end 280 of the loading device 2 of FIG. 34 is shown inserted into a flexible wall 260.

Figure 37:
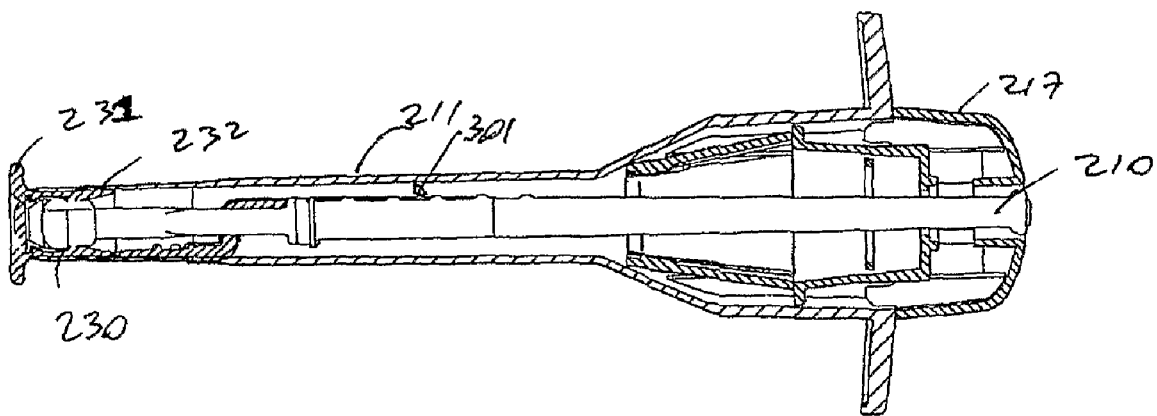

FIG. 37 is a cross-sectional view wherein the tool 210 from FIG. 34 is pushed further into the loading tube 211 and wherein the front flange 231 of the bushing 230 is pushed through the front end 280 of the loading tube 211, the front flange 231 being transversely unfolded.

Figure 15:
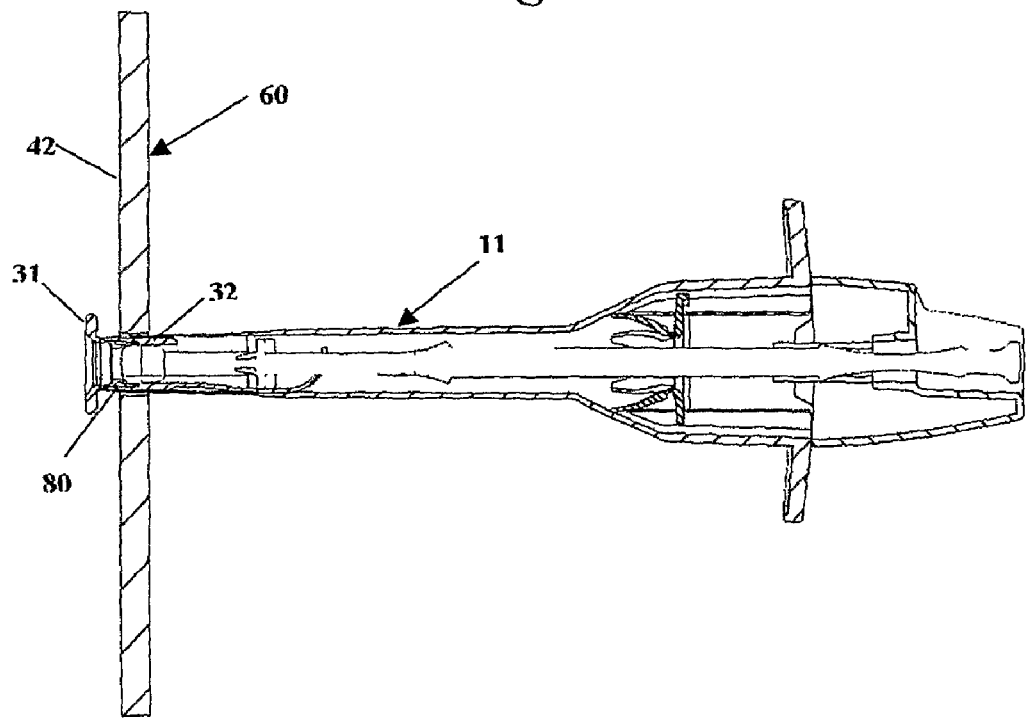
FIG. 15 is an axial cross-sectional view, wherein the front flange of the bushing is pushed through the front end of the loading tube, the front flange being transversely unfolded.
Figure 16:
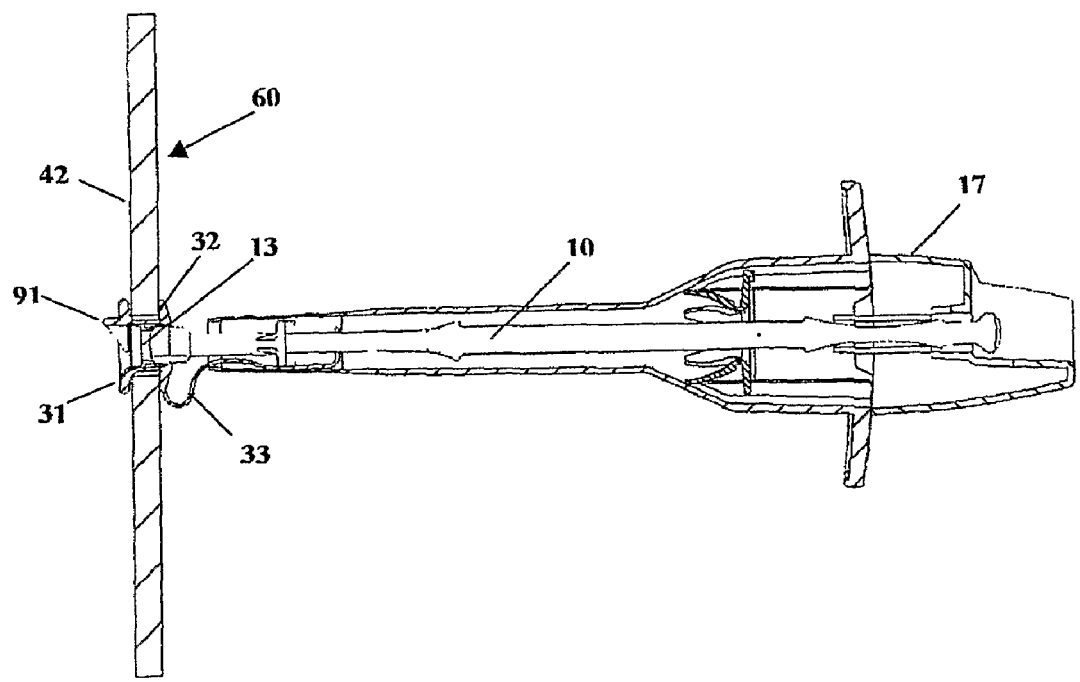
FIG. 16 is an axial cross-sectional view, wherein the bushing is released from the loading tube and the rear flange is transversely unfolded.
Figure 38:
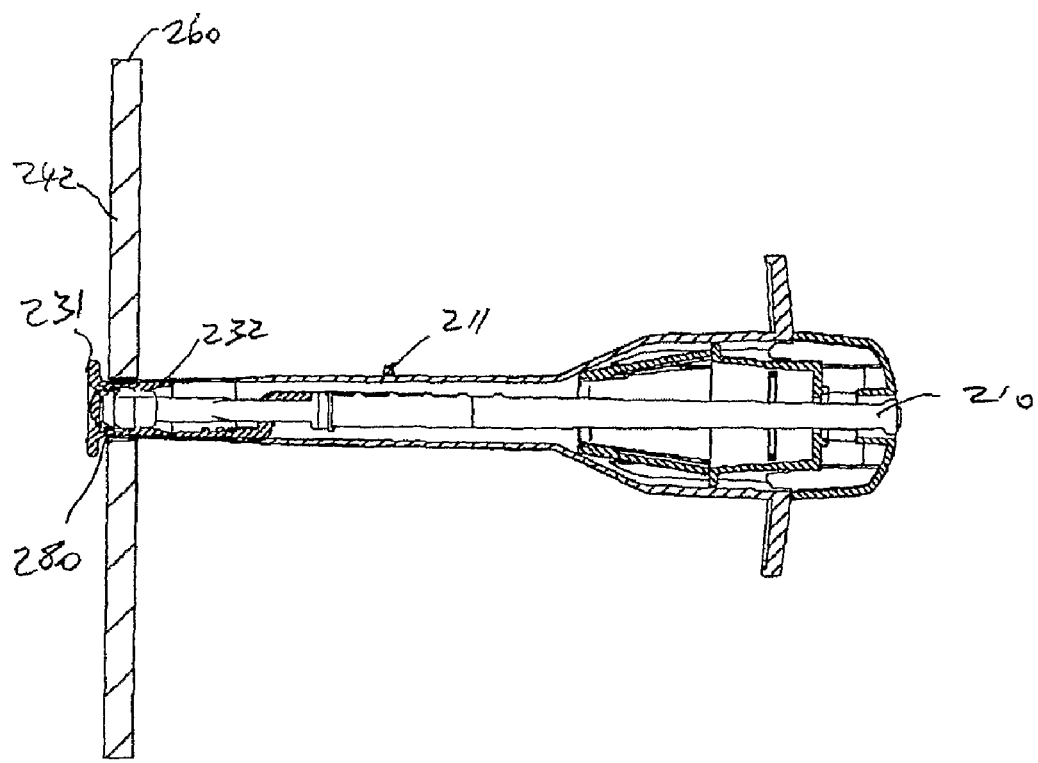

FIG. 38 corresponds FIG. 15 and illustrates in addition to FIG. 37 the flexible wall 260 in relation to the unfolded front flange 231.

Figure 39:
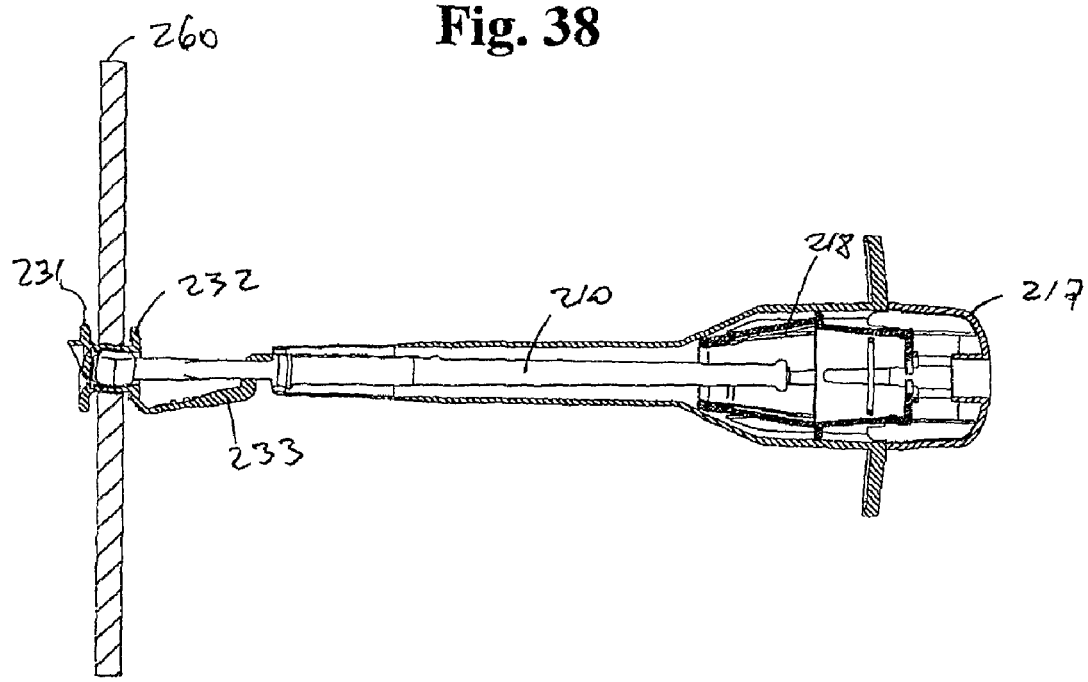

FIG. 39 corresponds FIG. 16 and is an axial cross-sectional view, wherein the bushing 230 is released from the loading tube 211 and the rear flange 232 is transversely unfolded on the other side of the wall 260.

Figure 17:
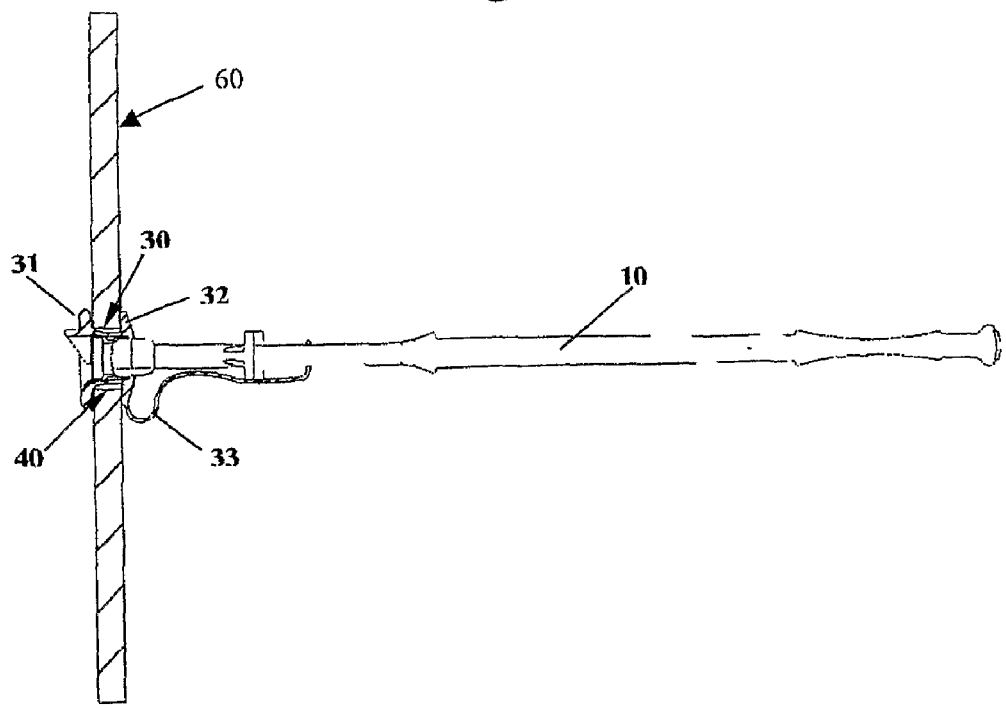
FIG. 17 is an axial cross-sectional view, wherein the loading tube assembly is removed.
Figure 40:
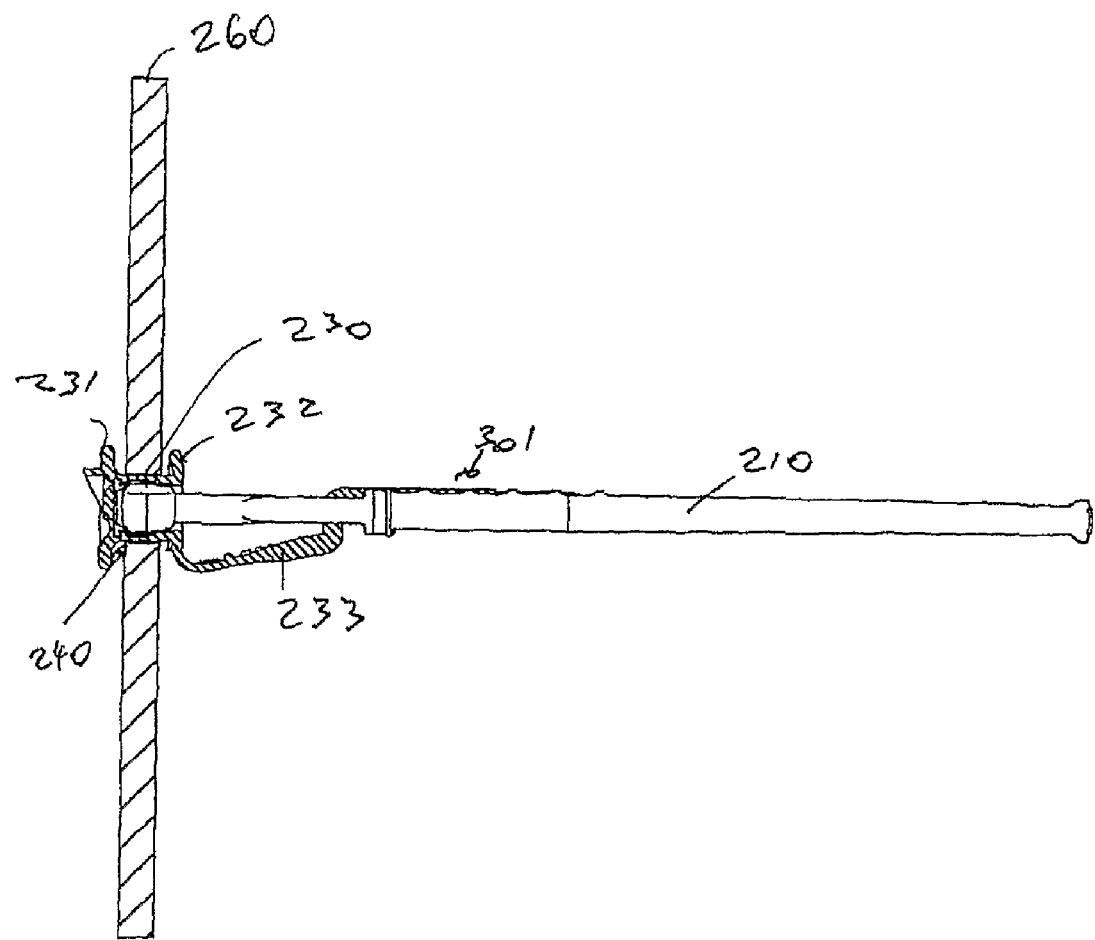

FIG. 40 corresponds FIG. 17 and is an axial cross-sectional view, wherein the loading tube assembly is removed and only the tool 210 is still attached to the bushing 230 inserted into wall 260, before the safety string 233 and the tool 210 are removed and the bushing is finally positioned into the wall 260.

In FIG. 29 the beginning of a sequence of bending flanges 231, 232 of bushing 230 initially oriented radially away from the main cylindrical body of bushing 230 is shown. In FIG. 30 the assembly comprising the bending member 218, which during the above assembly of the loading device has received bushing 230 in its central interior, is pushed forward in insertion direction 250 by pushing inserter 210 in said direction. Bending member is slidingly displaced in direction 250, but still interconnected by element 300. This movement causes wings 236 of bending member 218 to push flange 231 forward into the direction of the loading tube 211. When the wings 236 with its forward ends abut against the radially inclined interior wall of the introduction section 222 of the loading tube 211, the wings further push flange 231 axially forward and radially inwards into tube 211. Wings 236 are moveable, substantially in radial direction towards the central longitudinal axis of the loading device 2. By further pushing tool 210 forward in direction 250, the wings of bending member 218 are forced to move radially inward. This results consequently in a longitudinally forward and radially inward movement of flange 231, forwarding it into elongate loading tube segment 221, as depicted in FIGS. 32 and 33. By pushing inserter 210 further in insertion direction 250, the ring 235 of bending member 218 abuts against the interior wall of inclined section 222, thus stopping further displacement of bending member 218 in insertion direction 250. When inserter 210 is pushed even further in insertion direction 250, an increasing pushing force results in bushing 230 being pushed off the central passage of bending member 218. Bushing 230 is thus released from bending member 218 and is free for a subsequent forwarding into loading tube 211. Upon further displacement of tool 210, bushing 230 moves on in insertion direction 250, still attached to head 213, and thus together with tool 210. Flange 232 slips also out of bending member 218 and is bent axially backward, as seen in inserting direction 250.

Hence, flanges 231 and 232 are automatically bent into the shown orientations. There is no need for manually squeezing, pushing, folding, or for performing similar mechanical tasks on one of the flanges 231, 232 in order to achieve the orientation as shown in FIG. 33.

For facilitating displacement of the bushing 230 along the loading tube 211, the latter may be pre-lubricated internally or coated with a suitable material on the interior surface thereof.

In order to introduce the bushing into an aperture 240 in a flexible wall 260, which is accessible from one side 241 but not from the other side 242, the inserter 210 with the loading tube 211 and the bushing 230 is now pushed with tip 280 and as a unit through aperture 240 from wall side 241 in insertion direction 250, i.e. towards the left in the figures, resulting in the position as illustrated in FIG. 36. Alternatively, the tip 280 of the loading device 2 is inserted into aperture 40 prior to pushing forward inserter 10 from the position as shown in FIG. 29, and subsequently the above steps are performed arriving at the state illustrated in FIG. 36. By further pushing on end 119 of inserter 210, inserter 210 moves further in insertion direction, resulting in the position shown in FIG. 37 and FIG. 38 (with the wall 260).

In the following step, illustrated in FIG. 38, the inserter 210 and the bushing 230 are pushed forward in the loading tube 211, which is held stationary by the operator, so that flange 231 will be located outside the tip 280 of the loading tube 211. This position of the loading tube in relation to the inserter 210 is indicated to the operator at the back end of the loading device at guiding cover 217. There, the end 219 of inserter 210 is in register with the top of guiding cover 217, as illustrated on the right of FIG. 38. Thus, flange 231 is allowed to be unfolded on side 242 of wall 260. When this has taken place, the loading the loading tube and the bushing is withdrawn as a unit towards the right opposite to insertion direction 250, until flange 231 engages wall side 242. The pull applied to the loading device possibly being so great that wall 260 will be partly compressed. Due to anchoring by means of the anchoring security string 233 and also to some extent due to friction between the bushing and the head 213, if any, the bushing is prevented from sliding off the inserter 210. With the flange 231 thus engaged with the wall side 242 of the wall 260, the loading device is further withdrawn over inserter 210 in order to release also flange 232, so that it unfolds on the opposite wall side 241 of the flexible wall 260, as illustrated in FIG. 39.

Subsequently, the loading tube 211 is withdrawn completely from the inserter 210, see FIG. 40. Then, anchoring string 233 is disconnected from inserter 210, which is withdrawn from the bushing 230, which will then be left in wall 260 with the flanges 231, 232 projecting around the aperture 240 at opposite sides 231, 232 of the wall 260. Due to the flexible wall 260 being compressed between the flanges 231, 232 of bushing 230, a tight and stable attachment of the bushing 230 in the wall 260 will be secured. String 233 is cut off, and mounting of the bushing 230 in the aperture 240 is completed.

The inserter 210 must of course be adapted to the bushing 230 to be mounted in the flexible wall 260, similarly as inserter 10 described above.

As can be seen e.g. in FIG. 33, the tube end 280 is slotted. This may be in any of the forms described above in connection with FIGS. 18-20.

The elements of the loading device according to the invention may be provided in at least partly transparent material. In this case it is easily confirmed if the elements are correctly oriented in relation to each other, both during manufacturing and during insertion of the tubular element.

If the element to be mounted in a flexible wall is constructed as a voice prosthesis, which is to be mounted in a fistula in the tracheoesophageal wall, said wall and fistula correspond to wall 60 and aperture 40, respectively, in the illustrative examples.

The invention can be implemented in any suitable form within the scope of the appended claims. The elements and components of a embodiments of the invention may be physically, functionally and logically implemented in any suitable way. Indeed, the functionality may be implemented in a single unit, in a plurality of units or as part of other functional units. As such, the invention may be implemented in a single unit, or may be physically and functionally distributed between different units and assemblies.

Although the present invention has been described above with reference to specific embodiments, it is not intended to be limited to the specific form set forth herein. Rather, the invention is limited only by the accompanying claims and, other embodiments than the specific above are equally possible within the scope of these appended claims, e.g. different bending means or tool forms than those described above.

In the claims, the term "comprises/comprising" does not exclude the presence of other elements or steps. Furthermore, although individually listed, a plurality of means, elements or method steps may be implemented by e.g. a single unit or assembly. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

The invention claimed is:

1. A method for inserting a tubular element forming a central passage and having a retainer projecting transversely at each end thereof, said retainer being resiliently foldable towards the longitudinal axis of said tubular element, into a through-aperture in a flexible wall accessible from one side only, comprising the steps of:
    passing the element into a loading tube, the retainers being folded to project substantially axially from the ends of the element,
    inserting the loading tube with the element enclosed therein at one end of the tube through the aperture from said one side of the wall,
    partially withdrawing the loading tube, the element being held stationary by a tool inserted into the tube from the other end thereof so that the forward retainer as seen in the insertion direction will be released and will unfold at the other side of the wall,
    further withdrawing the loading tube while the element is being held stationary in order that the rear retainer as seen in the insertion direction will be unfolded at said one side of the wall, and
    withdrawing the loading tube and the tool from the element which is left in the aperture with the retainers located one at each side of the wall, wherein
    said step of passing said tubular element into said loading tube comprises the step of automatically displacing a first one of said retainers radially and axially into said folded position projecting substantially axially in direction of said longitudinal axis and in insertion direction from a first end of the tubular element by means of a bending member, said bending member comprising a disk or ring, a central axial passage for releasably receiving the tubular element, and wings such that the bending member may be at least partially maneuvered into the interior of the loading tube thereby compressing the wings and the retainer.

2. The method according to claim 1, wherein the tubular element is detachably mounted to said bending member further comprising the step of said bending member releasing said element when passing the element into said loading tube.

3. The method according to claim 2, wherein said tubular element is mounted to said tool at one end thereof before the step of passing the element into said loading tube.

4. The method according to claim 1, wherein the element during insertion thereof is held at a security string projecting from said tubular element.

5. The method according to claim 4, wherein said security string is anchored to said tool and preferably the security strings end is fastened in a recess in said tool in order to avoid occlusion of the loading tube when moving the element there through.

6. The method according to claim 1, wherein the unfolded forward retainer by withdrawal of the element is engaged with said other side of the wall.

7. The method according to claim 1, further comprising the step of decreasing a release force for releasing said element from said bending member when displacing a first one of said retainers radially and axially by means of said bending member into said folded position.

8. The method according to claim 1, wherein said tubular element is a voice prosthesis, said flexible wall is the tracheoesophageal wall and said through-aperture is a fistula in the tracheoesophageal wall.

9. A method of manufacturing a self-contained device for inserting a tubular element into a through-aperture in a flexible wall accessible from one side only, preferably to a method according to claim 1, said element forming a central passage and having a retainer projecting transversely at each end thereof, said retainer being resiliently foldable towards the longitudinal axis of said tubular element, whereby said tubular element is releasably loaded at least partly into a central passage of a bending member.

10. The method according to claim 9, wherein said retainers extending substantially radially outwards on each side of said bending means, providing a first assembly, mounting said assembly releasably to a tool at one end thereof, providing a second assembly, inserting said second assembly axially into a loading section of a loading tube, pushing a cover over said tool via a central passage in said cover, and attaching said cover to said loading section.

11. The method according to claim 9, further comprising the steps of:
    providing a first assembly by mounting said tubular element releasably to a tool at one end thereof,
    providing a second assembly by displaceable interconnecting a cover with said bending member by means of an interconnecting element,
    providing a third assembly by inserting said first assembly into said second assembly, wherein one of said retainers extending substantially radially outwards on one side of said bending member abutting to an end thereof, and by inserting said tool with said element mounted thereon via a central passage in said cover and said bending element, and
    inserting said third assembly axially into a loading section of a loading tube and attaching said cover to said loading section.

12. A self-contained device for inserting a tubular element into a through-aperture in a flexible wall accessible from one side only, said element forming a central passage and having a retainer projecting transversely at each end thereof, said retainer being resiliently foldable towards the longitudinal axis of said tubular element, said device comprising:
    a loading tube for receiving the tubular element therein with said retainers folded and projecting substantially axially from the element, said retainers folded by means of a bending member, said bending member comprising a disk or ring, a central axial passage for releasably receiving the tubular element, and wings such that the bending member may be at least partially maneuvered into the interior of the loading tube thereby compressing the wings and the retainers, and a tool to be received in the loading tube to be engaged with the element therein, said loading tube and said tool being relatively displaceable for pushing the element out of the loading tube; and an assembly including said tubular element releasably mounted to said tool at one end thereof, wherein said assembly is releasably attached to said bending member providing a further assembly, said further assembly being positioned in a loading section of said loading tube with said tool partly protruding out of a guide attached to said loading section.

13. The device according to claim 12, wherein said bending member having a central passage for releasably axially receiving said tubular element with said retainers substantially axially unbent, a rigid disk, and wings adapted to folding said retainers projecting axially from the element.

14. The device according to claim 12, wherein said bending member having a central interior for at least partly releasably axially receiving said tubular element with said retainers substantially axially unbent, a ring and wings adapted for pushing a first retainer axially from said element.

15. The device according to claim 12, wherein said bending member comprises keying elements with mating elements on the interior wall of said loading section of said loading tube, said keying elements ensuring a forward/rear-orientation of said bending member inside said device.

16. The device according to claim 12, wherein an end portion of said loading tube is radially resiliently expandable by pressure against the inside surface thereof, and a means for limiting the range of said radially outward movement of said end portion.

17. The device according to claim 16, wherein said end portion comprises flexible flaps curved towards the center of said end portion, said means being adapted to limit said radially outward movement of said flaps, such that the outside diameter of said end portion does not substantially exceed the inner diameter of an aperture in said flexible wall.

18. The device according to claim 16, wherein said means that is adapted to limit said radially outward movement comprises a hose of a resilient material passed circumferentially over said end portion, or a hose passed circumferentially over said end portion with foldings extending radially inward into longitudinal slots in said end portion, or such foldings being an integral part of said end portion.

* * * * *